(12) United States Patent
Peinado Pereira

(10) Patent No.: US 11,649,460 B2
(45) Date of Patent: May 16, 2023

(54) DNA APTAMERS, METHOD FOR INHIBITING HUMAN GALECTIN-1 AND METHOD OF TREATING A MAMMAL IN NEED THEREOF

(71) Applicants: Joao Francisco Peinado Pereira, Ribeirao Preto (BR); Daniel Pereira Pola, Rio de Janeiro (BR)

(72) Inventor: Joao Francisco Peinado Pereira, Ribeirao Preto (BR)

(73) Assignees: Joao Francisco Peinado Pereira, Ribeirao Preto (BR); Daniel Pereira Pola, Rio de Janeiro (BR)

( * ) Notice: Subject to any disclaimer, the term of this patent is extended or adjusted under 35 U.S.C. 154(b) by 13 days.

(21) Appl. No.: 16/825,284

(22) Filed: Mar. 20, 2020

(65) Prior Publication Data

US 2021/0301293 A1    Sep. 30, 2021

(51) Int. Cl.
  *C12N 15/115*    (2010.01)
  *A61K 45/06*     (2006.01)
  *A61K 31/713*    (2006.01)

(52) U.S. Cl.
  CPC .......... *C12N 15/115* (2013.01); *A61K 31/713* (2013.01); *A61K 45/06* (2013.01)

(58) Field of Classification Search
  None
  See application file for complete search history.

(56) References Cited

U.S. PATENT DOCUMENTS

| | | |
|---|---|---|
| 8,981,075 B2 | 3/2015 | Ikebukuro |
| 10,494,634 B2 | 12/2019 | Sheffield et al. |
| 2014/0121278 A1 | 5/2014 | Mayo |

FOREIGN PATENT DOCUMENTS

| | | |
|---|---|---|
| WO | 2014070214 A1 | 5/2014 |
| WO | 2014159669 A2 | 10/2014 |
| WO | 2017176767 A1 | 10/2017 |

OTHER PUBLICATIONS

Sundblad et al. The Journal of Immunology 199:3721-3730 (Year: 2017).*

Shih et al., "A Novel Galectin-1 inhibitor Discovered through One-Bead-Two-Compounds Library Potentiates the Anti-tumor Effects of Paclitaxel in vivo",American Association for Cancer Research Journal, 2017, pp. 1-14.

Ingrassia et al.,"Anti-Galectin Compounds as Potential Anti-Cancer Drugs",Current Medicinal Chemistry, 2006, vol. 13, No. 29, pp. 3513-3527.

Dings et al.,"Antitumor Agent Calixarene 0118 Targets Human Galectin-1 as an Allosteric Inhibitor of Carbohydrate Binding", J. Med. Chem., 2012, vol. 55, pp. 5121-5129.

Blanchard et al., "Galectin-1 inhibitors and their potential therapeutic applications: a patent review",Taylor & Francis Group, 2016, pp. 1-18.

Wdowiak et al., "Galectin Targeted Therapy in Oncology: Current Knowledge and Perspectives", Int. J. Mol. Sci., 2018, vol. 19, No. 210, pp. 1-21.

Ito et al., "Galectin-1 as a potent target for cancer therapy: role in the tumor microenvironment", Cancer Metastasis Rev, 2012, pp. 1-16.

Salatino et al., "Galectin-1 as a potential therapeutic target in autoimmune disorders and cancer", Expert Opin. Biol. Ther., 2008, vol. 8, No. 1, pp. 45-57.

Koonce et al., "Galectin-1 Inhibitor OTX008 Induces Tumor Vessel Normalization and Tumor Growth Inhibition in Human Head and Neck Squamous Cell Carcinoma Models", Int. J. Mol. Sci., 2017, vol. 18, No. 2671, pp. 1-9.

Blanchard et al., "Galectin-3 inhibitors: a patent review (2008-present)", Expert Opin. Ther. Patents, 2014, vol. 24, No. 10, pp. 1-13.

Dahlqvist et al., "Stereo- and regioselective hydroboration of 1-exomethylene pyranoses: discovery of aryltriazolylmethyl C-galactopyranosides as selective galectin-1 inhibitors", Beilstein J. Org. Chem., 2019, vol. 15, pp. 1046-1060.

Cousin et al., "The Role of Galectin-1 in Cancer Progression, and Synthetic Multivalent Systems for the Study of Galectin-1", Int. J. Mol. Sci., 2016, vol. 17, No. 1566, pp. 1-22.

* cited by examiner

*Primary Examiner* — Brian Whiteman
(74) *Attorney, Agent, or Firm* — Lucas & Mercanti, LLP

(57) ABSTRACT

DNA aptamers that recognize the human galectin-1 hGal1 with a very high degree of binding affinity and specificity, and inhibit hGal1-induced hemagglutination, besides presenting antiproliferative effects in seven human solid tumor cell lines are disclosed. The cytotoxicity tests demonstrated that, among 41 sequences tested, four of them (SEQ ID NO.: 04, SEQ ID NO.: 09, SEQ ID NO.:10 and, SEQ ID NO.:12) have the best capacity of inhibiting the cell growth in tumor cell. Additionally, the aptamers developed in the present invention will be used, for example, in the treatment of disorders related to the binding of human galectin-1 to a ligand in a mammal, wherein said disorder is selected from the group consisting of inflammation, fibrosis, septic shock, cancer, autoimmune diseases, metabolic disorders, heart disease, heart failure, pathological angiogenesis, and eye diseases, mainly cancer.

34 Claims, 19 Drawing Sheets

Specification includes a Sequence Listing.

SEQUENCE LISTING

<160> NUMBER OF SEQ ID NOS: 48

<210> SEQ ID NO 1
<211> LENGTH: 93
<212> TYPE: DNA
<213> ORGANISM: Artificial Sequence
<220> FEATURE:
<223> OTHER INFORMATION: Aptamer 1

<400> SEQUENCE: 1
agctgacaca gcaggttggt gcaaaatggt cgaaaaaagg aaaaaggaag ataagataat    60
aagaaaagga cccgagtcga gcaatctcga aat                                93

<210> SEQ ID NO 2
<211> LENGTH: 93
<212> TYPE: DNA
<213> ORGANISM: Artificial Sequence
<220> FEATURE:
<223> OTHER INFORMATION: Aptamer 2

<400> SEQUENCE: 2
agctgacaca gcaggttggt gctttttta ccctgggttt taagtttatt agaatcgtca     60
tactgaattt accgagtcga gcaatctcga aat                                93

<210> SEQ ID NO 3
<211> LENGTH: 92
<212> TYPE: DNA
<213> ORGANISM: Artificial Sequence
<220> FEATURE:
<223> OTHER INFORMATION: Aptamer 3
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 3
annganacag caggttggtg cctaaaacac ccccacacac aatccccgac cgacccaccg    60
cactgccacc ccgagtcgag caatctcgaa at                                 92

<210> SEQ ID NO 4
<211> LENGTH: 91
<212> TYPE: DNA
<213> ORGANISM: Artificial Sequence
<220> FEATURE:
<223> OTHER INFORMATION: Aptamer 4

<400> SEQUENCE: 4
ctgacacagc aggttggtgc caactaacac cataagaata ccccgctcca aataagccca    60
cacgtaaacc cgagtcgagc aatctcgaaa t                                  91

<210> SEQ ID NO 5
<211> LENGTH: 92
<212> TYPE: DNA
<213> ORGANISM: Artificial Sequence
<220> FEATURE:
<223> OTHER INFORMATION: Aptamer 5

<400> SEQUENCE: 5
agctgacaca gcaggttggt gcggaattaa gaacagaagg ggtagggaga agaccacgga    60
caagcaaaag ccgagtcgag caatctcgaa at                                 92

```
<210> SEQ ID NO 6
<211> LENGTH: 93
<212> TYPE: DNA
<213> ORGANISM: Artificial Sequence
<220> FEATURE:
<223> OTHER INFORMATION: Aptamer 6

<400> SEQUENCE: 6
agctgacaca gcaggttggt gcctctacac ccgtaagtac ctttgaccaa cggcactatt     60
caccatctga cccgagtcga gcaatctcga aat                                  93

<210> SEQ ID NO 7
<211> LENGTH: 92
<212> TYPE: DNA
<213> ORGANISM: Artificial Sequence
<220> FEATURE:
<223> OTHER INFORMATION: Aptamer 7

<400> SEQUENCE: 7
agctgacaca gcaggttggt gccaatggtg aatagaaaa agtatgtgta aggtggttgg      60
tgtgggttga ccgagtcgag caatctcgaa at                                   92

<210> SEQ ID NO 8
<211> LENGTH: 90
<212> TYPE: DNA
<213> ORGANISM: Artificial Sequence
<220> FEATURE:
<223> OTHER INFORMATION: Aptamer 8

<400> SEQUENCE: 8
agggaacagg aggttggtgc gcggaaagga aagggaagca aggaggagaa agaagaggag     60
tgaggactcc gagtcgagca atctcgaaat                                      90

<210> SEQ ID NO 9
<211> LENGTH: 93
<212> TYPE: DNA
<213> ORGANISM: Artificial Sequence
<220> FEATURE:
<223> OTHER INFORMATION: Aptamer 9

<400> SEQUENCE: 9
agctgacaca gcaggttggt gcccaaaaga gccaatccac gacgacaccc caaaaaccat     60
atcacgaata cccgagtcga gcaatctcga aat                                  93

<210> SEQ ID NO 10
<211> LENGTH: 93
<212> TYPE: DNA
<213> ORGANISM: Artificial Sequence
<220> FEATURE:
<223> OTHER INFORMATION: Aptamer 10

<400> SEQUENCE: 10
agctgacaca gcaggttggt gccaacaaga aaagaaaccg ttacagaaga cactacagaa     60
taagtgaaaa gccgagtcga gcaatctcga aat                                  93

<210> SEQ ID NO 11
<211> LENGTH: 92
<212> TYPE: DNA
<213> ORGANISM: Artificial Sequence
<220> FEATURE:
<223> OTHER INFORMATION: Aptamer 11
```

-continued

<400> SEQUENCE: 11
agctgacaca gcaggttggt gccatagccc acacatcacc gaacaaccgc cactagttca    60
acatcccatc ccgagtcgag caatctcgaa at    92

<210> SEQ ID NO 12
<211> LENGTH: 93
<212> TYPE: DNA
<213> ORGANISM: Artificial Sequence
<220> FEATURE:
<223> OTHER INFORMATION: Aptamer 12

<400> SEQUENCE: 12
agctgacaca gcaggttggt gcgcccaata caggcgcagt atctgtccgt gggccgggta    60
aaagttacgg accgagtcga gcaatctcga aat    93

<210> SEQ ID NO 13
<211> LENGTH: 93
<212> TYPE: DNA
<213> ORGANISM: Artificial Sequence
<220> FEATURE:
<223> OTHER INFORMATION: Aptamer 13

<400> SEQUENCE: 13
agctgacaca gcaggttggt gcttttaggg tcttgtttat agtcattgcc aatggttttt    60
gtttggatgg gccgagtcga gcaatctcga aat    93

<210> SEQ ID NO 14
<211> LENGTH: 152
<212> TYPE: DNA
<213> ORGANISM: Artificial Sequence
<220> FEATURE:
<223> OTHER INFORMATION: Aptamer 14

<400> SEQUENCE: 14
agctgacaca gcaggttggt gccaagacaa acgcaaaacc caccccacac ccacaaccaa    60
atcaccaaac ccccaatcca ggaatctcca ataacaacc atcaccactt ataccacctc    120
tttcccacct gcaccaacct ggtgtggcag ct    152

<210> SEQ ID NO 15
<211> LENGTH: 93
<212> TYPE: DNA
<213> ORGANISM: Artificial Sequence
<220> FEATURE:
<223> OTHER INFORMATION: Aptamer 15

<400> SEQUENCE: 15
agctgacaca gcaggttggt gccttaaaaa ccccaaaacc taaacaaatc cagacaaaaa    60
ctctcaccaa accgagtcga gcaatctcga aat    93

<210> SEQ ID NO 16
<211> LENGTH: 93
<212> TYPE: DNA
<213> ORGANISM: Artificial Sequence
<220> FEATURE:
<223> OTHER INFORMATION: Aptamer 16

<400> SEQUENCE: 16
agctgacaca gcaggttggt gccaacgcac actcaaaccc caccctcccc caagcctcgg    60
gcctaaataa tccgagtcga gcaatctcga aat    93

```
<210> SEQ ID NO 17
<211> LENGTH: 93
<212> TYPE: DNA
<213> ORGANISM: Artificial Sequence
<220> FEATURE:
<223> OTHER INFORMATION: Aptamer 17

<400> SEQUENCE: 17
agctgacaca gcaggttggt gccaaaaagg gagaaaaaaa aagaaaagaa caaaaaaaag      60
aaagaaataa accgagtcga gcaatctcga aat                                  93

<210> SEQ ID NO 18
<211> LENGTH: 93
<212> TYPE: DNA
<213> ORGANISM: Artificial Sequence
<220> FEATURE:
<223> OTHER INFORMATION: Aptamer 18

<400> SEQUENCE: 18
agctgacaca gcaggttggt gcccacccga caaccctccc tccccctaac tcccccctc      60 tacttttgca cccgagtcga gcaatctcga aat                                  93

<210> SEQ ID NO 19
<211> LENGTH: 93
<212> TYPE: DNA
<213> ORGANISM: Artificial Sequence
<220> FEATURE:
<223> OTHER INFORMATION: Aptamer 19

<400> SEQUENCE: 19
agctgacaca gcaggttggt gctcccacga tccccacata cctcctcccc actgctatac    60
agtacctacc cccgagtcga gcaatctcga aat                                  93

<210> SEQ ID NO 20
<211> LENGTH: 93
<212> TYPE: DNA
<213> ORGANISM: Artificial Sequence
<220> FEATURE:
<223> OTHER INFORMATION: Aptamer 20

<400> SEQUENCE: 20
agctgataca gcaggttaga ggaaaaaaga ataaaaaaaa aaataaaaaa tcgaacggaa    60
aaattaaaaa accgagtcga gcaatctcga aat                                  93

<210> SEQ ID NO 21
<211> LENGTH: 91
<212> TYPE: DNA
<213> ORGANISM: Artificial Sequence
<220> FEATURE:
<223> OTHER INFORMATION: Aptamer 21

<400> SEQUENCE: 21
atttagaggg gctcgactcg gactacaaag ccaaaagaaa tagaatagac gaagaaaaaa    60
aaccaaactg caccaacctg ctgtgtcagc t                                    91

<210> SEQ ID NO 22
<211> LENGTH: 92
<212> TYPE: DNA
<213> ORGANISM: Artificial Sequence
<220> FEATURE:
<223> OTHER INFORMATION: Aptamer 22
<220> FEATURE:
<221> NAME/KEY: misc_feature
<222> LOCATION: (5)..(5)
```

<223> OTHER INFORMATION: n is a, c, g, or t

<400> SEQUENCE: 22
atttngagat tgctcgactc gggatgggat gttgaactag tggcggttgt tcggtgatgt    60
gtgggctatg gcaccaacct gctgtgtcag ct                                  92

<210> SEQ ID NO 23
<211> LENGTH: 93
<212> TYPE: DNA
<213> ORGANISM: Artificial Sequence
<220> FEATURE:
<223> OTHER INFORMATION: Aptamer 23

<400> SEQUENCE: 23
atttcgagat tgctcgactc gggtttacgt gtgggcttat ttggagcggg gtattcttat    60
ggtgttagtt ggcaccaacc tgctgtgtca gct                                 93

<210> SEQ ID NO 24
<211> LENGTH: 93
<212> TYPE: DNA
<213> ORGANISM: Artificial Sequence
<220> FEATURE:
<223> OTHER INFORMATION: Aptamer 24

<400> SEQUENCE: 24
atttcgagat tgctcgactc ggcccatcca acaaaaaacc attggcaatg actataaaca    60
agaccctaaa agcaccaacc tgctgtgtca gct                                 93

<210> SEQ ID NO 25
<211> LENGTH: 93
<212> TYPE: DNA
<213> ORGANISM: Artificial Sequence
<220> FEATURE:
<223> OTHER INFORMATION: Aptamer 25
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 25
atttngagnt tgntcgactc gggtattcgt gatatggttt ttggggagac gacgtggatt    60
ggctcttttg ggcaccaacc tgctgtgtca gct                                 93

<210> SEQ ID NO 26
<211> LENGTH: 93
<212> TYPE: DNA
<213> ORGANISM: Artificial Sequence
<220> FEATURE:
<223> OTHER INFORMATION: Aptamer 26

<400> SEQUENCE: 26
atttcgagat tgctcgactc ggcttttcac ttattctgta gtgtcttctg taacggtttc    60
ttttcttgtt ggcaccaacc tgctgtgtca gct                                 93

<210> SEQ ID NO 27
<211> LENGTH: 93

<212> TYPE: DNA
<213> ORGANISM: Artificial Sequence
<220> FEATURE:
<223> OTHER INFORMATION: Aptamer 27

<400> SEQUENCE: 27
atttagagat tgctcgactc ggtccgtaac ttttacccgg cccacggaca gatactgcgc    60
ctgtattggg cgcaccaacc tgctgtgtca gct                                 93

<210> SEQ ID NO 28
<211> LENGTH: 93
<212> TYPE: DNA
<213> ORGANISM: Artificial Sequence
<220> FEATURE:
<223> OTHER INFORMATION: Aptamer 28

<400> SEQUENCE: 28
atttcgagat tgctcgactc gggttgggga gagttttgt ctggatttgt ttaggttttg     60
gggtttttaa ggcaccaacc tgctgtgtca gct                                 93

<210> SEQ ID NO 29
<211> LENGTH: 93
<212> TYPE: DNA
<213> ORGANISM: Artificial Sequence
<220> FEATURE:
<223> OTHER INFORMATION: Aptamer 29

<400> SEQUENCE: 29
atttcgagat tgctcgactc ggattattta ggcccgaggc ttgggggagg gtgggtttg     60 agtgtgcgtt ggcaccaacc tgctgtgtca gct                                 93

<210> SEQ ID NO 30
<211> LENGTH: 93
<212> TYPE: DNA
<213> ORGANISM: Artificial Sequence
<220> FEATURE:
<223> OTHER INFORMATION: Aptamer 30
<220> FEATURE:
<221> NAME/KEY: misc_feature
<222> LOCATION: (4)..(4)
<223> OTHER INFORMATION: n is a, c, g, or t

<400> SEQUENCE: 30
attncgagat tgctcgactc ggtttatttc tttctttttt ttgttttttt cttttttttt    60
ctcccttttt ggcaccaacc tgctgtgtca gct                                 93

<210> SEQ ID NO 31
<211> LENGTH: 93
<212> TYPE: DNA
<213> ORGANISM: Artificial Sequence
<220> FEATURE:
<223> OTHER INFORMATION: Aptamer 31
<220> FEATURE:
<221> NAME/KEY: misc_feature
<222> LOCATION: (5)..(5)
<223> OTHER INFORMATION: n is a, c, g, or t

<400> SEQUENCE: 31
atttngagat tgctcgactc gggtgatgag gcttctgtag gggtactaag tcaggtgcag    60
agtttgagtt ggcaccaacc tgctgtgtca gct                                 93

<210> SEQ ID NO 32
<211> LENGTH: 93
<212> TYPE: DNA

```
<213> ORGANISM: Artificial Sequence
<220> FEATURE:
<223> OTHER INFORMATION: Aptamer 32
<220> FEATURE:
<221> NAME/KEY: misc_feature
<222> LOCATION: (5)..(5)
<223> OTHER INFORMATION: n is a, c, g, or t

<400> SEQUENCE: 32
atttngagat tgctcgactc gggtgcaaaa gtagagggg ggagttaggg ggagggaggg      60
ttgtcgggtg ggcaccaacc tgctgtgtca gct                                 93

<210> SEQ ID NO 33
<211> LENGTH: 93
<212> TYPE: DNA
<213> ORGANISM: Artificial Sequence
<220> FEATURE:
<223> OTHER INFORMATION: Aptamer 33
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 33
attncgagnt tgctcgactc gggggaaggt actgtatagc aggggggagg agggatgtgg    60
ggatcgtggg agcaccaacc tgctgtgtca gct                                 93

<210> SEQ ID NO 34
<211> LENGTH: 93
<212> TYPE: DNA
<213> ORGANISM: Artificial Sequence
<220> FEATURE:
<223> OTHER INFORMATION: Aptamer 34

<400> SEQUENCE: 34
attgggagat tgctcgactc ggttttttaa ttttccgtt cgtttttta tttttttttt      60 tattcttttt ggcaccaacc tgctgtgtca gct                                 93

<210> SEQ ID NO 35
<211> LENGTH: 93
<212> TYPE: DNA
<213> ORGANISM: Artificial Sequence
<220> FEATURE:
<223> OTHER INFORMATION: Aptamer 35

<400> SEQUENCE: 35
atttcgagat tgctcgactc gggtcctttt cttattatct tatcttcctt tttccttttt    60
tcgaccattt tgcaccaacc tgctgtgtca gct                                 93

<210> SEQ ID NO 36
<211> LENGTH: 93
<212> TYPE: DNA
<213> ORGANISM: Artificial Sequence
<220> FEATURE:
<223> OTHER INFORMATION: Aptamer 36

<400> SEQUENCE: 36
atttcgagat tgctcgactc ggtaaattca gtatgacgat tctaataaac ttaaaaccca    60
gggtaaaaaa agcaccaacc tgctgtgtca gct                                 93
```

```
<210> SEQ ID NO 37
<211> LENGTH: 93
<212> TYPE: DNA
<213> ORGANISM: Artificial Sequence
<220> FEATURE:
<223> OTHER INFORMATION: Aptamer 37

<400> SEQUENCE: 37
atttcgagat tgctcgactc ggggtggcag tgcggtgggt cggtcgggga ttgtgtgtgg    60
gggtgtttta ggcaccaacc tgctgtgtca gct                                93

<210> SEQ ID NO 38
<211> LENGTH: 92
<212> TYPE: DNA
<213> ORGANISM: Artificial Sequence
<220> FEATURE:
<223> OTHER INFORMATION: Aptamer 38

<400> SEQUENCE: 38
atttcgagat tgctcgactc ggcttttgct tgtctgtggt cttctcccta cccttctgt    60 tcttaattcc gcaccaacct gctgtgtcag ct                                 92

<210> SEQ ID NO 39
<211> LENGTH: 92
<212> TYPE: DNA
<213> ORGANISM: Artificial Sequence
<220> FEATURE:
<223> OTHER INFORMATION: Aptamer 39
<220> FEATURE:
<221> NAME/KEY: misc_feature
<222> LOCATION: (4)..(5)
<223> OTHER INFORMATION: n is a, c, g, or t

<400> SEQUENCE: 39
attnnagatt gctcgactcg ggtcagatgg tgaatagtgc cgttggtcaa aggtacttac    60
gggtgtagag gcaccaacct gctgtgtcag ct                                 92

<210> SEQ ID NO 40
<211> LENGTH: 92
<212> TYPE: DNA
<213> ORGANISM: Artificial Sequence
<220> FEATURE:
<223> OTHER INFORMATION: Aptamer 40

<400> SEQUENCE: 40
atttcgagat tgctcgactc ggtcaaccca caccaaccac cttacacata cttttctat    60 tccaccattg gcaccaacct gctgtgtcag ct                                 92

<210> SEQ ID NO 41
<211> LENGTH: 92
<212> TYPE: DNA
<213> ORGANISM: Artificial Sequence
<220> FEATURE:
<223> OTHER INFORMATION: Aptamer 41

<400> SEQUENCE: 41
atttcgagat tgagcaaaac ggagtcctca ctcctctgct ttctcctcct tgcttccctt    60
ccctttccgc gcaccaacct gctgtgtcac ct                                 92

<210> SEQ ID NO 42
<211> LENGTH: 134
<212> TYPE: PRT
<213> ORGANISM: Artificial Sequence
<220> FEATURE:
```

<223> OTHER INFORMATION: Human galectin-1 (hGal1)

<400> SEQUENCE: 42

Ala Cys Gly Leu Val Ala Ser Asn Leu Asn Leu Lys Pro Gly Glu Cys
1               5                   10                  15

Leu Arg Val Arg Gly Glu Val Ala Pro Asp Ala Lys Ser Phe Val Leu
            20                  25                  30

Asn Leu Gly Lys Asp Ser Asn Asn Leu Cys Leu His Phe Asn Pro Arg
        35                  40                  45

Phe Asn Ala His Gly Asp Ala Asn Thr Ile Val Cys Asn Ser Lys Asp
    50                  55                  60

Gly Gly Ala Trp Gly Thr Glu Gln Arg Glu Ala Val Phe Pro Phe Gln
65                  70                  75                  80

Pro Gly Ser Val Ala Glu Val Cys Ile Thr Phe Asp Gln Ala Asn Leu
                85                  90                  95

Thr Val Lys Leu Pro Asp Gly Tyr Glu Phe Lys Phe Pro Asn Arg Leu
            100                 105                 110

Asn Leu Glu Ala Ile Asn Tyr Met Ala Ala Asp Gly Asp Phe Lys Ile
        115                 120                 125

Lys Cys Val Ala Phe Asp
    130

<210> SEQ ID NO 43
<211> LENGTH: 93
<212> TYPE: DNA
<213> ORGANISM: Artificial Sequence
<220> FEATURE:
<223> OTHER INFORMATION: library and primer
<220> FEATURE:
<221> NAME/KEY: misc_feature
<222> LOCATION: (23)..(71)
<223> OTHER INFORMATION: n is a, c, g, or t

<400> SEQUENCE: 43
agctgacaca gcaggttggt gcnnnnnnnn nnnnnnnnnn nnnnnnnnnn nnnnnnnnnn    60
nnnnnnnnnn nccgagtcga gcaatctcga aat                                 93

<210> SEQ ID NO 44
<211> LENGTH: 22
<212> TYPE: DNA
<213> ORGANISM: Artificial Sequence
<220> FEATURE:
<223> OTHER INFORMATION: forward primer

<400> SEQUENCE: 44
agctgacaca gcaggttggt gc                                             22

<210> SEQ ID NO 45
<211> LENGTH: 22
<212> TYPE: DNA
<213> ORGANISM: Artificial Sequence
<220> FEATURE:
<223> OTHER INFORMATION: reverse primer

<400> SEQUENCE: 45
atttcgagat tgctcgactc gg                                             22

<210> SEQ ID NO 46
<211> LENGTH: 96
<212> TYPE: DNA
<213> ORGANISM: Artificial Sequence
<220> FEATURE:

```
<223> OTHER INFORMATION: Aptamer formula (1)
<220> FEATURE:
<221> NAME/KEY: misc_feature
<222> LOCATION: (23)..(23)
<223> OTHER INFORMATION: n is a, t, c, g or absent
<220> FEATURE:
<221> NAME/KEY: misc_feature
<222> LOCATION: (24)..(27)
<223> OTHER INFORMATION: n is a, t, c or g
<220> FEATURE:
<221> NAME/KEY: misc_feature
<222> LOCATION: (28)..(34)
<223> OTHER INFORMATION: n is a, t, c, g or absent
<220> FEATURE:
<221> NAME/KEY: misc_feature
<222> LOCATION: (35)..(37)
<223> OTHER INFORMATION: n is a, t, c or g
<220> FEATURE:
<221> NAME/KEY: misc_feature
<222> LOCATION: (38)..(40)
<223> OTHER INFORMATION: n is a, t, c, g or absent
<220> FEATURE:
<221> NAME/KEY: misc_feature
<222> LOCATION: (41)..(47)
<223> OTHER INFORMATION: n is a, t, c or g
<220> FEATURE:
<221> NAME/KEY: misc_feature
<222> LOCATION: (48)..(48)
<223> OTHER INFORMATION: n is a, t, c, g or absent
<220> FEATURE:
<221> NAME/KEY: misc_feature
<222> LOCATION: (49)..(49)
<223> OTHER INFORMATION: n is a, t, c or g
<220> FEATURE:
<221> NAME/KEY: misc_feature
<222> LOCATION: (50)..(50)
<223> OTHER INFORMATION: n is a, t, c, g or absent
<220> FEATURE:
<221> NAME/KEY: misc_feature
<222> LOCATION: (51)..(51)
<223> OTHER INFORMATION: n is a, t, c, g or absent
<220> FEATURE:
<221> NAME/KEY: misc_feature
<222> LOCATION: (52)..(53)
<223> OTHER INFORMATION: n is a, t, c or g
<220> FEATURE:
<221> NAME/KEY: misc_feature
<222> LOCATION: (54)..(54)
<223> OTHER INFORMATION: n is a, t, c, g or absent
<220> FEATURE:
<221> NAME/KEY: misc_feature
<222> LOCATION: (55)..(55)
<223> OTHER INFORMATION: n is a, t, c or g
<220> FEATURE:
<221> NAME/KEY: misc_feature
<222> LOCATION: (56)..(58)
<223> OTHER INFORMATION: n is a, t, c, g or absent
<220> FEATURE:
<221> NAME/KEY: misc_feature
<222> LOCATION: (59)..(61)
<223> OTHER INFORMATION: n is a, t, c or g
<220> FEATURE:
<221> NAME/KEY: misc_feature
<222> LOCATION: (62)..(64)
<223> OTHER INFORMATION: n is a, t, c, g or absent
<220> FEATURE:
<221> NAME/KEY: misc_feature
<222> LOCATION: (65)..(67)
<223> OTHER INFORMATION: n is a, t, c or g
<220> FEATURE:
<221> NAME/KEY: misc_feature
<222> LOCATION: (68)..(68)
<223> OTHER INFORMATION: n is a, t, c or absent
<220> FEATURE:
<221> NAME/KEY: misc_feature
<222> LOCATION: (69)..(69)
<223> OTHER INFORMATION: n is t, c, g or absent
<220> FEATURE:
<221> NAME/KEY: misc_feature
```

<222> LOCATION: (70)..(74)
<223> OTHER INFORMATION: n is a, t, c, g or absent

<400> SEQUENCE: 46
agctgacaca gcaggttggt gcnnnnnnnn nnnnnnnnnn nnnnnnnnnn nnnnnnnnnn    60
nnnnnnnnnn nnnnccgagt cgagcaatct cgaaat    96

<210> SEQ ID NO 47
<211> LENGTH: 92
<212> TYPE: DNA
<213> ORGANISM: Artificial Sequence
<220> FEATURE:
<223> OTHER INFORMATION: Aptamer formula (2)
<220> FEATURE:
<221> NAME/KEY: misc_feature
<222> LOCATION: (23)..(23)
<223> OTHER INFORMATION: n is c or absent
<220> FEATURE:
<221> NAME/KEY: misc_feature
<222> LOCATION: (24)..(24)
<223> OTHER INFORMATION: n is a, c or g
<220> FEATURE:
<221> NAME/KEY: misc_feature
<222> LOCATION: (25)..(26)
<223> OTHER INFORMATION: n is a or c
<220> FEATURE:
<221> NAME/KEY: misc_feature
<222> LOCATION: (27)..(27)
<223> OTHER INFORMATION: n is a, c or t
<220> FEATURE:
<221> NAME/KEY: misc_feature
<222> LOCATION: (28)..(28)
<223> OTHER INFORMATION: n is a or g
<220> FEATURE:
<221> NAME/KEY: misc_feature
<222> LOCATION: (29)..(29)
<223> OTHER INFORMATION: n is a, c or t
<220> FEATURE:
<221> NAME/KEY: misc_feature
<222> LOCATION: (30)..(30)
<223> OTHER INFORMATION: n is a or g
<220> FEATURE:
<221> NAME/KEY: misc_feature
<222> LOCATION: (31)..(32)
<223> OTHER INFORMATION: n is a or c
<220> FEATURE:
<221> NAME/KEY: misc_feature
<222> LOCATION: (33)..(33)
<223> OTHER INFORMATION: n is a or g
<220> FEATURE:
<221> NAME/KEY: misc_feature
<222> LOCATION: (34)..(34)
<223> OTHER INFORMATION: n is a, g or t
<220> FEATURE:
<221> NAME/KEY: misc_feature
<222> LOCATION: (35)..(35)
<223> OTHER INFORMATION: n is a, t, c, g or absent
<220> FEATURE:
<221> NAME/KEY: misc_feature
<222> LOCATION: (36)..(36)
<223> OTHER INFORMATION: n is a, c or g
<220> FEATURE:
<221> NAME/KEY: misc_feature
<222> LOCATION: (37)..(37)
<223> OTHER INFORMATION: n is c or g
<220> FEATURE:
<221> NAME/KEY: misc_feature
<222> LOCATION: (38)..(38)
<223> OTHER INFORMATION: n is a or c
<220> FEATURE:
<221> NAME/KEY: misc_feature
<222> LOCATION: (39)..(39)
<223> OTHER INFORMATION: n is a, c or g
<220> FEATURE:
<221> NAME/KEY: misc_feature
<222> LOCATION: (40)..(40)

```
<223> OTHER INFORMATION: n is g or t
<220> FEATURE:
<221> NAME/KEY: misc_feature
<222> LOCATION: (41)..(41)
<223> OTHER INFORMATION: n is a or t
<220> FEATURE:
<221> NAME/KEY: misc_feature
<222> LOCATION: (42)..(42)
<223> OTHER INFORMATION: n is a, c or t
<220> FEATURE:
<221> NAME/KEY: misc_feature
<222> LOCATION: (43)..(43)
<223> OTHER INFORMATION: n is c or g
<220> FEATURE:
<221> NAME/KEY: misc_feature
<222> LOCATION: (44)..(44)
<223> OTHER INFORMATION: n is a, c or t
<220> FEATURE:
<221> NAME/KEY: misc_feature
<222> LOCATION: (45)..(45)
<223> OTHER INFORMATION: n is c or g
<220> FEATURE:
<221> NAME/KEY: misc_feature
<222> LOCATION: (46)..(46)
<223> OTHER INFORMATION: n is a, g or t
<220> FEATURE:
<221> NAME/KEY: misc_feature
<222> LOCATION: (47)..(47)
<223> OTHER INFORMATION: n is a or c
<220> FEATURE:
<221> NAME/KEY: misc_feature
<222> LOCATION: (48)..(48)
<223> OTHER INFORMATION: n is c, g or t
<220> FEATURE:
<221> NAME/KEY: misc_feature
<222> LOCATION: (49)..(49)
<223> OTHER INFORMATION: n is a, c or g
<220> FEATURE:
<221> NAME/KEY: misc_feature
<222> LOCATION: (50)..(50)
<223> OTHER INFORMATION: n is c or t
<220> FEATURE:
<221> NAME/KEY: misc_feature
<222> LOCATION: (51)..(51)
<223> OTHER INFORMATION: n is a or g
<220> FEATURE:
<221> NAME/KEY: misc_feature
<222> LOCATION: (52)..(52)
<223> OTHER INFORMATION: n is a, c or g
<220> FEATURE:
<221> NAME/KEY: misc_feature
<222> LOCATION: (53)..(53)
<223> OTHER INFORMATION: n is a, g or t
<220> FEATURE:
<221> NAME/KEY: misc_feature
<222> LOCATION: (54)..(54)
<223> OTHER INFORMATION: n is a, c or t
<220> FEATURE:
<221> NAME/KEY: misc_feature
<222> LOCATION: (55)..(55)
<223> OTHER INFORMATION: n is a or c
<220> FEATURE:
<221> NAME/KEY: misc_feature
<222> LOCATION: (56)..(56)
<223> OTHER INFORMATION: n is a, c or g
<220> FEATURE:
<221> NAME/KEY: misc_feature
<222> LOCATION: (57)..(57)
<223> OTHER INFORMATION: n is c or g
<220> FEATURE:
<221> NAME/KEY: misc_feature
<222> LOCATION: (58)..(58)
<223> OTHER INFORMATION: n is a, c or g
<220> FEATURE:
<221> NAME/KEY: misc_feature
<222> LOCATION: (59)..(60)
<223> OTHER INFORMATION: n is a, c or t
<220> FEATURE:
<221> NAME/KEY: misc_feature
```

```
<222> LOCATION: (61)..(61)
<223> OTHER INFORMATION: n is a or t
<220> FEATURE:
<221> NAME/KEY: misc_feature
<222> LOCATION: (62)..(62)
<223> OTHER INFORMATION: n is a or c
<220> FEATURE:
<221> NAME/KEY: misc_feature
<222> LOCATION: (63)..(63)
<223> OTHER INFORMATION: n is a or g
<220> FEATURE:
<221> NAME/KEY: misc_feature
<222> LOCATION: (64)..(64)
<223> OTHER INFORMATION: n is c, g or t
<220> FEATURE:
<221> NAME/KEY: misc_feature
<222> LOCATION: (65)..(65)
<223> OTHER INFORMATION: n is g or t
<220> FEATURE:
<221> NAME/KEY: misc_feature
<222> LOCATION: (66)..(66)
<223> OTHER INFORMATION: n is a or t
<220> FEATURE:
<221> NAME/KEY: misc_feature
<222> LOCATION: (67)..(67)
<223> OTHER INFORMATION: n is c or absent
<220> FEATURE:
<221> NAME/KEY: misc_feature
<222> LOCATION: (68)..(68)
<223> OTHER INFORMATION: n is a, g or t
<220> FEATURE:
<221> NAME/KEY: misc_feature
<222> LOCATION: (69)..(69)
<223> OTHER INFORMATION: n is a or g
<220> FEATURE:
<221> NAME/KEY: misc_feature
<222> LOCATION: (70)..(70)
<223> OTHER INFORMATION: n is a, c or g

<400> SEQUENCE: 47
agctgacaca gcaggttggt gcnnnnnnnn nnnnnnnnnn nnnnnnnnnn nnnnnnnnnn        60
nnnnnnnnnn ccgagtcgag caatctcgaa at                                      92

<210> SEQ ID NO 48
<211> LENGTH: 93
<212> TYPE: DNA
<213> ORGANISM: Artificial Sequence
<220> FEATURE:
<223> OTHER INFORMATION: Aptamer of formula (3)
<220> FEATURE:
<221> NAME/KEY: misc_feature
<222> LOCATION: (23)..(24)
<223> OTHER INFORMATION: n are a, t, c, g or absent
<220> FEATURE:
<221> NAME/KEY: misc_feature
<222> LOCATION: (25)..(26)
<223> OTHER INFORMATION: n are a, t, c or g
<220> FEATURE:
<221> NAME/KEY: misc_feature
<222> LOCATION: (27)..(28)
<223> OTHER INFORMATION: n are a, t, c, g or absent
<220> FEATURE:
<221> NAME/KEY: misc_feature
<222> LOCATION: (29)..(36)
<223> OTHER INFORMATION: n is a, t, c or g
<220> FEATURE:
<221> NAME/KEY: misc_feature
<222> LOCATION: (37)..(37)
<223> OTHER INFORMATION: n are a, t, c, g or absent
<220> FEATURE:
<221> NAME/KEY: misc_feature
<222> LOCATION: (38)..(42)
<223> OTHER INFORMATION: n is a, t, c or g
<220> FEATURE:
<221> NAME/KEY: misc_feature
<222> LOCATION: (43)..(43)
```

```
<223> OTHER INFORMATION: n is c, g or t
<220> FEATURE:
<221> NAME/KEY: misc_feature
<222> LOCATION: (44)..(45)
<223> OTHER INFORMATION: n are a, t, c, g or absent
<220> FEATURE:
<221> NAME/KEY: misc_feature
<222> LOCATION: (46)..(55)
<223> OTHER INFORMATION: n is a, t, c or g
<220> FEATURE:
<221> NAME/KEY: misc_feature
<222> LOCATION: (56)..(57)
<223> OTHER INFORMATION: n are a, t, c, g or absent
<220> FEATURE:
<221> NAME/KEY: misc_feature
<222> LOCATION: (58)..(68)
<223> OTHER INFORMATION: n is a, t, c or g
<220> FEATURE:
<221> NAME/KEY: misc_feature
<222> LOCATION: (69)..(69)
<223> OTHER INFORMATION: n is a, g or t
<220> FEATURE:
<221> NAME/KEY: misc_feature
<222> LOCATION: (70)..(70)
<223> OTHER INFORMATION: n is a, t, c or g
<220> FEATURE:
<221> NAME/KEY: misc_feature
<222> LOCATION: (71)..(73)
<223> OTHER INFORMATION: n are a, t, c, g or absent

<400> SEQUENCE: 48
atttcgagat tgctcgactc ggnnnnnnnn nnnnnnnnnn nnnnnnnnnn nnnnnnnnnn      60
nnnnnnnnnn ngcaccaacc tgctgtgtca gct                                  93
```

DNA APTAMERS, METHOD FOR INHIBITING HUMAN GALECTIN-1 AND METHOD OF TREATING A MAMMAL IN NEED THEREOF

SEQUENCE LISTING

The sequence listing of the present application has been submitted electronically via EFS-Web as an ASCII formatted sequence listing with a file name SubstituteSequence-Listing.txt, creation date of Apr. 8, 2020 and a size of 13 KB. The sequence listing is part of the specification and is herein incorporated by reference in its entirety.

INCORPORATION BY REFERENCE OF SEQUENCE LISTING

The contents of the text file named "SubstituteSequence-Listing.txt," which was created on Dec. 20, 2021 and is 20.1 KB in size, are hereby incorporated by reference in their entirety.

FIELD OF THE INVENTION

The present invention relates to the field of medicine, and more precisely, to the area of nucleic acids, and describes DNA aptamers that recognize human galectin-1 (hGal1) with a very high degree of binding affinity and specificity and inhibit hGal1-induced hemagglutination, besides presenting antiproliferative effect in tumor cell lines. The aptamers developed in the present invention will be used in the treatment of disorders related to the binding of human galectin-1 to a ligand in a mammal, wherein said disorder is selected from the group consisting of inflammation, fibrosis, septic shock, cancer, autoimmune diseases, metabolic disorders, heart disease, heart failure, pathological angiogenesis, and eye diseases, mainly cancer.

BACKGROUNDS OF THE INVENTION

Galectins are glycan-binding protein which preferably interacts with β-galactosides carbohydrates encounter both in O and N-linked polysaccharide. Galectin binding activity is generally due to its site in the carbohydrate recognition domain (CRD) which is evolutionarily conserved. Human galectin-1 (hGal1) contains a single CRD of about 15 kDa, which can homodimerize that increase the binding valency. It is among the better-studied galectins and its physiological roles are known to be involved in angiogenesis, leukocytes homeostasis and survival, modulation of host immune response including pathogen defense, fertility, inflammatory and autoimmune disorders. For example, hGal1 functions are of great interest in cancer biology because for it has been reported to be upregulated in different kinds of tumor cells and promotes multivalent protein-carbohydrate interactions that participate in multiple events of malignant cellular processes. In addition, hGal1 was described as an antitumor immune response suppressor, as a tumor angiogenesis inducer and as a promoter of the tumor metastasis process. Due to these activities involved in tumor development, galectin-1 is admitted as a promising target for anticancer therapy and continuous efforts are undertaken in the development of innovative galectin-1 binding molecules for therapeutic and diagnostic applications.

Lately, several technological advances have allowed the improvement of in vitro evolutionary methods for the identification of non-biological oligonucleotides that binds to such targets. This oligonucleotide in vitro evolutionary method for the selection of functional nucleic acids was called SELEX, and the new class of short single-stranded oligonucleotides ligands generated by this technique was called aptamers.

As used herein, the term "nucleotide" refers to a ribonucleotide or a deoxyribonucleotide, or a modified form thereof, as well as an analog thereof. Nucleotides include species that include purines (e.g., adenine, hypoxanthine, guanine, and their derivatives and analogs) as well as pyrimidines (e.g., cytosine, uracil, thymine, and their derivatives and analogs). When a base is indicated as "A", "C", "G", "U", or "T", it is intended to encompass both ribonucleotides and deoxyribonucleoties, and modified forms and analogs thereof.

As used herein, "nucleic acid", "oligonucleotide", and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included. The terms "polynucleotide", "oligonucleotide", and "nucleic acid" include double- or single stranded molecules as well as triple-helical molecules. Nucleic acid, oligonucleotide, and polynucleotide are broader terms than the term aptamer and, thus, the terms nucleic acid, oligonucleotide, and polynucleotide include polymers of nucleotides that are aptamers, but the terms nucleic acid, oligonucleotide, and polynucleotide are not limited to aptamers.

Aptamers are an individual class of molecules that in a similar way of antibodies, can be crafted to bind to many different targets and are, thus, useful as research tools in disease diagnostic and therapeutic. Furthermore, they are considerably superior to their competitors, such as monoclonal antibodies and other types of molecules, since they have a higher degree of affinity and specificity than other technologies, in addition to be synthetic, and consequently have a faster and inexpensive process.

The three-dimensional structure of both proteins and single strand DNA (ssDNA) aptamers plays a crucial role for their specific interaction, and target proteins can recognize the chemical signature of DNA aptamers sequence as well as the intrinsic aptamer three-dimensional structure (shape recognition). These sequence-shape recognition mechanisms do not exist alone but, relying on the individual interaction partners, are combined with various extents. Concerning ssDNA aptamers, the structures, and conformations adopted by ssDNA molecule, both influenced by and influencing the specific interaction with its corresponding target protein binding partner.

Biochemical, biophysical and structural studies on DNA and DNA-protein complexes have provided penetrating insights into how DNA sequence impacts on the structural and physical properties of this macromolecule and hence enables or prevents protein recognition. On the molecular level, whether a DNA protein complex is formed is determined by its free energy and the enthalpic and entropic gain and cost associated with each particular interaction. The DNA sequence determines and enables not only distinct interactions but also the overall conformational space occupied by the DNA and therefore its shape. Besides base-specific interactions between the target protein and ssDNA aptamers, one can observe that proteins recognize and stabilize DNA shapes.

The target protein associated with ssDNA aptamer via both hydrophobic stacking and ionic backbone interactions, and it is frequently observed that parts of the primers belong to the minimal binding motif and have at least some structural function. Therefore, it is possible to achieve, for the same target protein, ssDNA aptamers sequences with slight variations in the oligonucleotide sequence, but with the same or highly similar tertiary structure, thus having a significant affinity to the same target protein.

Most of the galectin-1 antagonists reported to date are β-galactoside-analogues or glycomimetics, therefore targeting the evident canonical carbohydrate-binding site. Most of these carbohydrate-based compounds designed to antagonize galectins, when in vitro evaluated, bind various of them with high kD values, like the 1-methyl derivative of LacNac, which has a Kd value of 70 µM. Besides, the human galectin-1 specificity of any of them remains an issue of importance, essentially due to the conserved structural homology of β-galactoside binding sites among all galectins.

Furthermore, these saccharide-based compounds are very unlikely to exhibit satisfactory performance in therapy when tested in vivo, mainly because of their hydrolysis susceptibility and fast clearance.

Due to the link between galectin-1, the progression of cancer and the escape of the immune system, this protein is a potential target for immunotherapy. Therefore, the development of a new class of inhibitors, such as DNA aptamers, is of great relevance.

In the development of the present invention, a single-step procedure approach was taken to identify specific aptamers that target the human galectin-1 (hGal1), represented here as SEQ ID NO. 42: ACGLVASNLN LKPGECLRVR GEVAP-DAKSF VLNLGKDSNN LCLHFNPRFN AHGDANTIVC NSKDGGAWGT EQREAVFPFQ PGSVAEVCIT FDQANLTVKL PDGYEFKFPN RLNLEAINYM AADGDFKIKC VAFD. Moreover, a Thermal Shift Assay (TSA) was used to confirm that hGal1 is, indeed, a protein target of selected aptamer and, further, by fluorescence quenching of the tryptophan residues that one of these aptamers interacts with this lectin. It has been revealed that an identified aptamer has functional inhibitory activity as they attenuate galectin-1-mediated cell agglutination. Hence, the described results suggest a favorable circumstance for exploiting the complex of hGal1 and a new aptamer as innovative therapeutic/diagnostic strategies. As can be seen below in the detailed description, the cytotoxicity tests demonstrated that SEQ ID NO.: 04, SEQ ID NO.: 09, SEQ ID NO.:10 and, SEQ ID NO.:12 have the capacity of inhibiting the cell growth in tumor cells.

PRIOR ARTS

Some prior art documents describe the use of aptamers and Galectin in the immunotherapy of cancer, for example:

The document entitled "A DNA APTAMER TARGETING GALECTIN-1 AS A NOVEL IMMUNOTHERAPEUTIC STRATEGY FOR LUNG CANCER, presents relevant information about the importance of Galectin-1 in immunotherapy against cancer. In addition, it is revealed in this document about the use of specific DNA aptamers that target Galectin-1. Still, it is revealed in this document about the SELEX protocol. Although this document is also based on DNA aptamers selected against the same protein target described (galectin-1) and for the same purpose in cancer immunotherapy, some important differences can be observed between the present application and the said document, such as the nucleotide sequence, the three dimensional structure, the size and the target site of the molecule. Such document describes that the aptamer developed has no cytotoxic effect for the tumor line tested, namely lung cancer. The molecules of the present invention, on the other hand, demonstrated to have a tumor growth-inhibiting effect for the cell lines tested so far. Therefore, the present application presents a broader spectrum and this results in a departure from the teachings of said prior art document. In addition, the oligonucleotide sequence described bears no resemblance to those of the present application, neither in alignment nor in size, and further the predicted interaction site between the aptamer and the target protein are also not the same. Consequently, given that the present invention reveals specific tests and results, specific quantities and concentrations, sequences with unique formation and purposes, as well as stages that were developed and elaborated for each of the tests to culminate in the sequences revealed herein, it would be possible for one skilled in the art to understand that the present application and said document teach away from each other.

The document entitled "POTENTIAL AND CHALLENGES OF APTAMERS AS SPECIFIC CARRIERS OF THERAPEUTIC OLIGONUCLEOTIDES FOR PRECISION MEDICINE IN CANCER", presents information related to the progress in the strategy mediated by aptamers in therapy. In addition, this document reports on the production of an aptamer-ASO chimera that is capable of silencing Galectin-1. As can be observed, such document is also a review, and although it describes the application of aptamers in cancer therapy, it has no specific association with the molecules of the present invention. In addition, the proposed therapy associated with galectin-1 aims at suppressing its expression, a fact unrelated to the invention in question.

The document entitled "BINDING OF GALECTIN-1 TO BREAST CANCER CELLS MCF7 INDUCES APOPTOSIS AND INHIBITION OF PROLIFERATION IN VITRO IN A 2D- AND 3D-CELL CULTURE MODEL", presents information regarding the general prior art. This document reveals information about Galectin-1 (Gal-1) and the possibilities of connections and events resulting from connections in (Gal-1). It is also described that such events can be used to treat cancer. However, such document proposes the application of galectin-1 as an antitumor agent, literally the opposite of the present invention, which proposes to suppress the action of galectin-1 in order to minimize the growth and metastasis of tumors.

The document "USE OF A GALECTIN-1-TARGETED RNAI-BASED APPROACH FOR THE TREATMENT OF CANCER", discloses the general prior art, in which it is described about the development of treatment methods for cancer. Additionally, it is revealed about the reduction of Galectin-1 expression, since it is related to tumor progression. Although the objective mentioned in such document is the same as that of the present invention, i.e., to suppress the action of galectin-1 overexpressed by tumor cells, the proposed technology is that of interfering RNA for silencing protein expression, having no direct correlation with the invention.

Therefore, as can be seen, there is no document in the state of the art that fully describes the object of the present invention, that is, it is understood that the invention has distinctive features, since no sequences were found to be similar or exactly described to the ones of the present invention. In addition, the development stages of the applied methodology for the preparation of the described aptamers were not found, exactly as revealed in the present invention. Still, no information was found about the concentrations and parameters of AptaGlal1 as established in the present invention, as well as relevant information about the inhibition of Galectin-1, hemagglutination and the prevention of multivalent interactions.

SUMMARY OF THE INVENTION

The present invention has the purpose of providing novel and unprecedented DNA aptamers that recognize hGal1 with a very high degree of binding affinity and specificity, and inhibit hGal1-induced hemagglutination, besides presenting antiproliferative effects in seven human solid tumor cell lines. These DNA aptamers were identified and selected from a library of synthetic aptamers using a modified SELEX protocol. Such aptamers were characterized using DNA sequence, thermal exchange assay, fluorescence spectroscopy, and had their biological function assessed by hemagglutination inhibition assay and by cell proliferation assay. The cytotoxicity tests demonstrated that SEQ ID NO.: 04, SEQ ID NO.: 09, SEQ ID NO.:10 and, SEQ ID NO.:12 have the capacity of inhibiting the cell growth in tumor cells.

Finally, in view of the discovery of such DNA aptamers, there is the possibility of developing new diagnostic strategies and therapeutic strategies for diseases correlated with hGal1, as those selected from the group consisting of inflammation, fibrosis, septic shock, cancer, autoimmune diseases, metabolic disorders, heart disease, heart failure, pathological angiogenesis, as neovascularization related to cancer, and eye diseases.

BRIEF DESCRIPTION OF THE FIGURES

In order to obtain a complete and full overview of the object of this invention, reference figures are presented, as follows:

FIG. 1 shows the Analysis of interaction between hGal1 and AptaGal1 by Thermal Shift Assay (TSA) and Fluorescence methods, wherein

FIG. 2 shows the Inhibitory effect on hemagglutination promoted by aptamer SEQ ID NO.: 4, wherein

FIG. 14 illustrates the physicochemical complementarity in the putative binding mode between hGal-1 and aptamer 4. The protein is shown as a solvent accessible surface colored according to the electrostatic potential in which blue represents +1 kT/e or more, white is zero potential and red is −1 kT/e or less. Galactose is shown as yellow spheres, Glucose is shown as orange spheres and the aptamer is shown as green cartoon. Wherein

DETAILED DESCRIPTION OF THE INVENTION

Figure 1A:
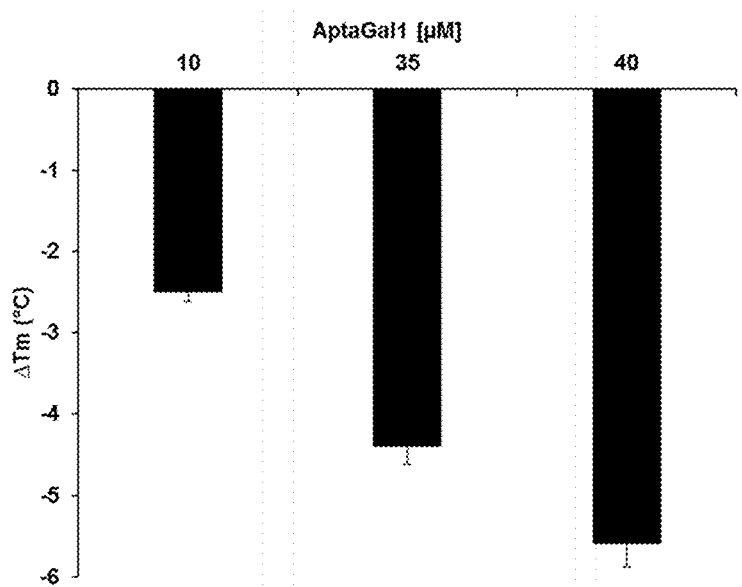
FIG. 1A represents the Tm variation and FIG. 1B represents the thermal displacement profile at melting temperature of the native galectin-1 human as a function of aptamer concentration. 0-40 μM of SEQ ID NO.: 4 were incubated with 5 μM of hGal1, and fluorescence was monitored by Sypro Orange fluorescence upon thermal denaturation of gal1. Decrease in thermal stability of native hGal1 was observed. Figure C represents the Fluorescence Emission Spectra of hGal1 when it was titrated with 0 to 7.2 μM of aptamer. All concentrations reduced the intensity of fluorescence of hGal1. Figure D represents the Plotter of fluorescence quenching caused by aptmer SEQ ID NO.: 4 versus aptamer log concentration. The apparent KD and the interacting number sites were estimated by Stern-Volmer equation, $\log((F0-F)/F)=\log(1/kd)+n\cdot\log Q$.
Figure 1B:
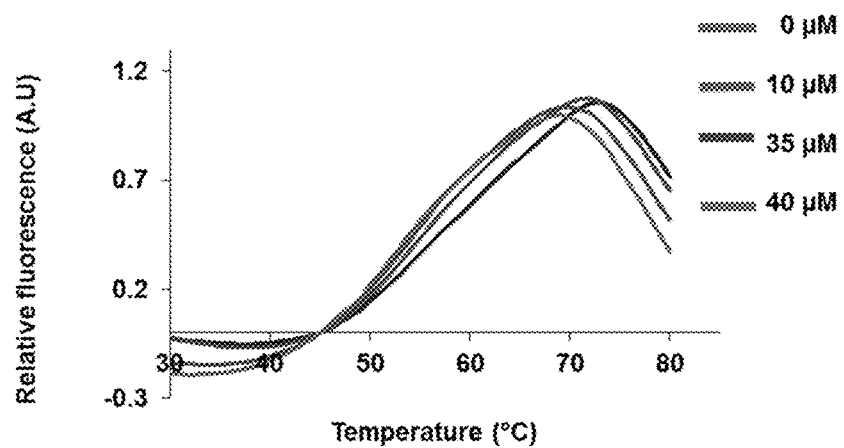

The present invention relates to DNA aptamers that recognize hGal1 with a very high degree of binding affinity and specificity, and inhibit hGal1-induced hemagglutination, besides presenting antiproliferative effect in tumor lines. Said aptamers were identified and selected from a library of synthetic aptamers using a modified SELEX protocol and furthermore were characterized using DNA sequence, thermal exchange assay, fluorescence spectroscopy and hemagglutination inhibition assay.

The structure of said aptamers is a three-dimensional structure. Said structure plays a crucial role for their specific interaction and functioning of their molecule, since that it allows a target protein recognize the chemical signature of DNA aptamers sequence as well as the intrinsic aptamer structure (shape recognition).

Said aptamers consist of a variable central region, flanked by two sites of primers interaction, denominated primers forward and reverse, which have the sequences 5'-AGC TGA CAC AGC AGG TTG GTG-3' and 5'-ATT TCG AGATTG CTC GAC TCG TG-3', respectively, and were selected from the following SEQ IDs.:

```
SEQ ID NO. 1:
AGCTGACACAGCAGGTTGGTGCAAAATGGTCGAAAAAAGGAAAAAGGAAGATAAGATAA
TAAGAAAAGGACCCGAGTCGAGCAATCTCGAAAT

SEQ ID NO. 2:
AGCTGACACAGCAGGTTGGTGCTTTTTTTACCCTGGGTTTTAAGTTTATTAGAATCGTC
ATACTGAATTTACCGAGTCGAGCAATCTCGAAAT

SEQ ID NO. 3:
ANNGANACAGCAGGTTGGTGCCTAAAACACCCCCACACACAATCCCCGACCGACCCACC
GCACTGCCACCCCGAGTCGAGCAATCTCGAAAT

SEQ ID NO. 4:
CTGACACAGCAGGTTGGTGCCAACTAACACCATAAGAATACCCCGCTCCAAATAAGCCC
ACACGTAAACCCGAGTCGAGCAATCTCGAAAT

SEQ ID NO. 5:
AGCTGACACAGCAGGTTGGTGCGGAATTAAGAACAGAAGGGGTAGGGAGAAGACCACGG
ACAAGCAAAAGCCGAGTCGAGCAATCTCGAAAT

SEQ ID NO. 6:
AGCTGACACAGCAGGTTGGTGCCTCTACACCCGTAAGTACCTTTGACCAACGGCACTAT
TCACCATCTGACCCGAGTCGAGCAATCTCGAAAT

SEQ ID NO. 7
AGCTGACACAGCAGGTTGGTGCCAATGGTGGAATAGAAAAAGTATGTGTAAGGTGGTTG
GTGTGGGTTGACCGAGTCGAGCAATCTCGAAAT

SEQ ID NO. 8:
AGGGAACAGGAGGTTGGTGCGCGGAAAGGAAAGGGAAGCAAGGAGGAGAAAGAAGAGGA
GTGAGGACTCCGAGTCGAGCAATCTCGAAAT

SEQ ID NO. 9:
AGCTGACACAGCAGGTTGGTGCCCAAAAGAGCCAATCCACGACGACACCCCAAAAACCA
TATCACGAATACCCGAGTCGAGCAATCTCGAAAT

SEQ ID NO. 10:
AGCTGACACAGCAGGTTGGTGCCAACAAGAAAAGAAACCGTTACAGAAGACACTACAGA
ATAAGTGAAAAGCCGAGTCGAGCAATCTCGAAAT

SEQ ID NO. 11:
AGCTGACACAGCAGGTTGGTGCCATAGCCCACACATCACCGAACAACCGCCACTAGTTC
AACATCCCATCCCGAGTCGAGCAATCTCGAAAT
```

-continued

SEQ ID NO. 12:
AGCTGACACAGCAGGTTGGTGCGCCCAATACAGGCGCAGTATCTGTCCGTGGGCCGGGT
AAAAGTTACGGACCGAGTCGAGCAATCTCGAAAT

SEQ ID NO. 13:
AGCTGACACAGCAGGTTGGTGCTTTTAGGGTCTTGTTTATAGTCATTGCCAATGGTTTT
TGTTTGGATGGGCCGAGTCGAGCAATCTCGAAAT

SEQ ID NO. 14:
AGCTGACACAGCAGGTTGGTGCCAAGACAAACGCAAAACCCACCCCACACCCACAACCA
AATCACCAAACCCCAATCCAGGAATCTCCAAATAACAACCATCACCACTTATACCACC
TCTTTCCCACCTGCACCAACCTGGTGTGGCAGCT

SEQ ID NO. 15:
AGCTGACACAGCAGGTTGGTGCCTTAAAAACCCCAAAACCTAAACAAATCCAGACAAAA
ACTCTCACCAAACCGAGTCGAGCAATCTCGAAAT

SEQ ID NO. 16:
AGCTGACACAGCAGGTTGGTGCCAACGCACACTCAAACCCCACCCTCCCCCAAGCCTCG
GGCCTAAATAATCCGAGTCGAGCAATCTCGAAAT

SEQ ID NO. 17:
AGCTGACACAGCAGGTTGGTGCCAAAAAGGGAGAAAAAAAAAGAAAAGAACAAAAAAAA
GAAAGAAATAAACCGAGTCGAGCAATCTCGAAAT

SEQ ID NO. 18:
AGCTGACACAGCAGGTTGGTGCCCACCCGACAACCCTCCCTCCCCCCTAACTCCCCCCCT
CTACTTTTGCACCCGAGTCGAGCAATCTCGAAAT

SEQ ID NO. 19:
AGCTGACACAGCAGGTTGGTGCTCCCACGATCCCCACATACCTCCTCCCCACTGCTATA
CAGTACCTACCCCCGAGTCGAGCAATCTCGAAAT

SEQ ID NO. 20:
AGCTGATACAGCAGGTTAGAGGAAAAAAGAATAAAAAAAAAAATAAAAAATCGAACGGA
AAAATTAAAAAACCGAGTCGAGCAATCTCGAAAT

SEQ ID NO. 21:
ATTTAGAGGGGCTCGACTCGGACTACAAAGCCAAAAGAAATAGAATAGACGAAGAAAAA
AAACCAAACTGCACCAACCTGCTGTGTCAGCT

SEQ ID NO. 22:
ATTTNGAGATTGCTCGACTCGGGATGGGATGTTGAACTAGTGGCGGTTGTTCGGTGATG
TGTGGGCTATGGCACCAACCTGCTGTGTCAGCT

SEQ ID NO. 23:
ATTTCGAGATTGCTCGACTCGGGTTTACGTGTGGGCTTATTTGGAGCGGGGTATTCTTA
TGGTGTTAGTTGGCACCAACCTGCTGTGTCAGCT

SEQ ID NO. 24:
ATTTCGAGATTGCTCGACTCGGCCCATCCAAACAAAAACCATTGGCAATGACTATAAAC
AAGACCCTAAAAGCACCAACCTGCTGTGTCAGCT

SEQ ID NO. 25:
ATTTNGAGNTTGNTCGACTCGGGTATTCGTGATATGGTTTTTGGGGAGACGACGTGGAT
TGGCTCTTTTGGGCACCAACCTGCTGTGTCAGCT

SEQ ID NO. 26:
ATTTCGAGATTGCTCGACTCGGCTTTTCACTTATTCTGTAGTGTCTTCTGTAACGGTTT
CTTTTCTTGTTGGCACCAACCTGCTGTGTCAGCT

SEQ ID NO. 27:
ATTTAGAGATTGCTCGACTCGGTCCGTAACTTTTACCCGGCCCACGGACAGATACTGCG
CCTGTATTGGGCGCACCAACCTGCTGTGTCAGCT

SEQ ID NO. 28:
ATTTCGAGATTGCTCGACTCGGGTTGGGGAGAGTTTTTGTCTGGATTTGTTTAGGTTTT
GGGGTTTTTAAGGCACCAACCTGCTGTGTCAGCT

SEQ ID NO. 29:
ATTTCGAGATTGCTCGACTCGGATTATTTAGGCCCGAGGCTTGGGGGAGGGTGGGGTTT
GAGTGTGCGTTGGCACCAACCTGCTGTGTCAGCT

SEQ ID NO. 30:
ATTNCGAGATTGCTCGACTCGGTTTATTTCTTTCTTTTTTTTGTTTTTTTCTTTTTTTT
TCTCCCTTTTTGGCACCAACCTGCTGTGTCAGCT

SEQ ID NO. 31:
ATTTNGAGATTGCTCGACTCGGGTGATGAGGCTTCTGTAGGGGTACTAAGTCAGGTGCA
GAGTTTGAGTTGGCACCAACCTGCTGTGTCAGCT

SEQ ID NO. 32:
ATTTNGAGATTGCTCGACTCGGGTGCAAAAGTAGAGGGGGGAGTTAGGGGAGGGAGG
GTTGTCGGGTGGGCACCAACCTGCTGTGTCAGCT

SEQ ID NO. 33:
ATTNCGAGNTTGCTCGACTCGGGGGAAGGTACTGTATAGCAGGGGGGAGGAGGGATGTG
GGGATCGTGGGAGCACCAACCTGCTGTGTCAGCT

SEQ ID NO. 34:
ATTGGGAGATTGCTCGACTCGGTTTTTTAATTTTTCCGTTCGTTTTTTTATTTTTTTTT
TTATTCTTTTTGGCACCAACCTGCTGTGTCAGCT

SEQ ID NO. 35:
ATTTCGAGATTGCTCGACTCGGGTCCTTTTCTTATTATCTTATCTTCCTTTTTCCTTTT
TTCGACCATTTTGCACCAACCTGCTGTGTCAGCT

SEQ ID NO. 36:
ATTTCGAGATTGCTCGACTCGGTAAATTCAGTATGACGATTCTAATAAACTTAAAACCC
AGGGTAAAAAAAGCACCAACCTGCTGTGTCAGCT

SEQ ID NO. 37:
ATTTCGAGATTGCTCGACTCGGGGTGGCAGTGCGGTGGGTCGGTCGGGGATTGTGTGTG
GGGGTGTTTTAGGCACCAACCTGCTGTGTCAGCT

SEQ ID NO. 38:
ATTTCGAGATTGCTCGACTCGGCTTTTGCTTGTCTGTGGTCTTCTCCCTACCCCTTCTG
TTCTTAATTCCGCACCAACCTGCTGTGTCAGCT

SEQ ID NO. 39:
ATTNNAGATTGCTCGACTCGGGTCAGATGGTGAATAGTGCCGTTGGTCAAAGGTACTTA
CGGGTGTAGAGGCACCAACCTGCTGTGTCAGCT

SEQ ID NO. 40:
ATTTCGAGATTGCTCGACTCGGTCAACCCACACCAACCACCTTACACATACTTTTCTA
TTCCACCATTGGCACCAACCTGCTGTGTCAGCT

SEQ ID NO. 41:
ATTTCGAGATTGAGCAAAACGGAGTCCTCACTCCTCTGCTTTCTCCTCCTTGCTTCCCT
TCCCTTTCCGCGCACCAACCTGCTGTGTCACCT

Figure 15:
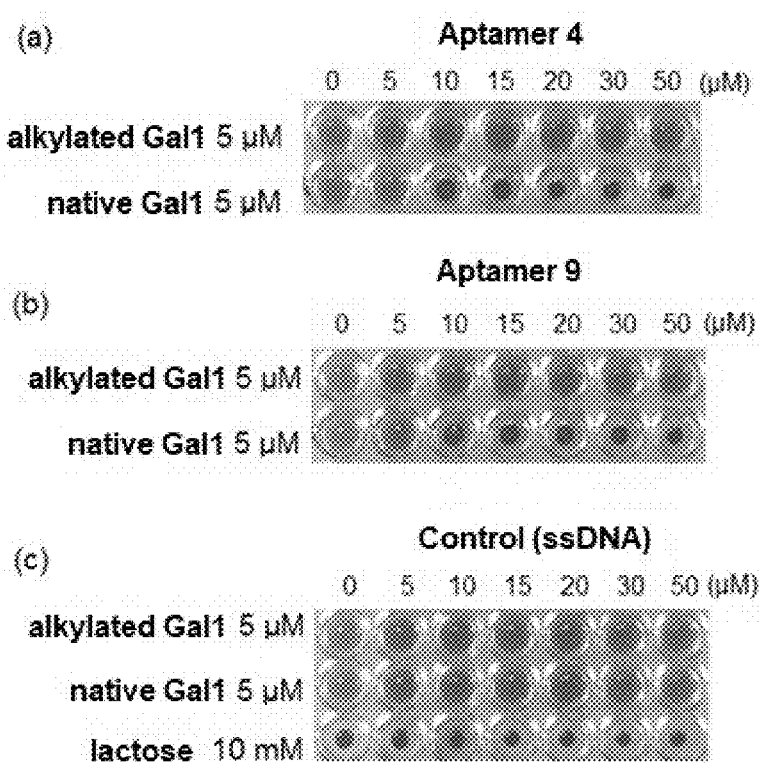
FIG. 15 illustrates the hemagglutination test with constant protein concentration at 5 µM and titration of aptamers SEQ ID NO.: 4 and SEQ ID NO.: 9. (a) Titration with aptamer 4. The hemagglutination of native Gal1 was inhibited from the concentration of 10 µM of this compound. There was no observed effect on the alkylated Gal1; (b) Titration with aptamer SEQ ID NO.: 9. Hemagglutination was also inhibited from the concentration of 10 µM of the compound and there was no effect on the alkylated Gal1; (c) Titration with random single stranded DNA sequences. No inhibitory effect was observed. Lactose (positive control) inhibited hemagglutinating activity as expected.
Figure 16:
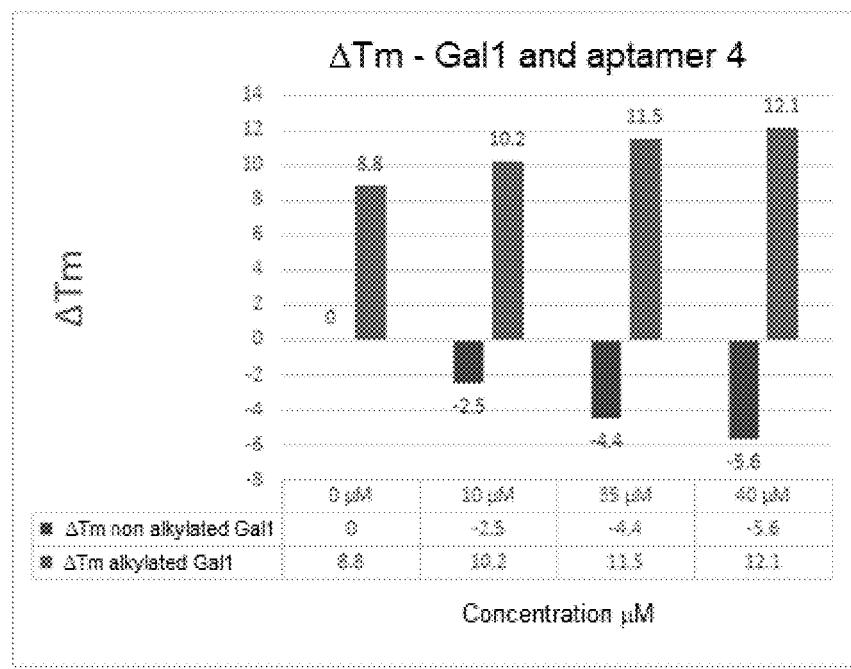
FIG. 16 illustrates the variations in the denaturation temperature caused by aptamer 4. The ΔTm caused by the interaction of aptamer SEQ ID NO.: 4 with native galectin (red bars) and alkylated galectin (blue bars), in different concentrations of aptamer (0 µM, 10 µM, 35 µM, 40 µM). The lectin concentration was 5 µM in all measures.
Figure 17:
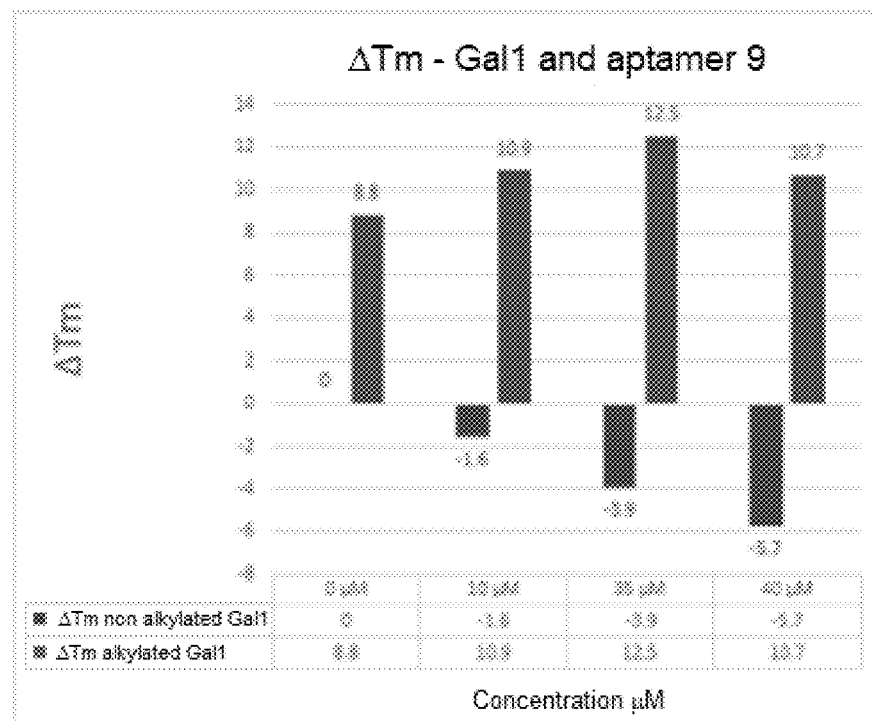
FIG. 17 illustrates the variations in the denaturation temperature caused by aptamer SEQ ID NO.: 9. The ΔTm caused by the interaction of aptamer SEQ ID NO.: 4 with native galectin (red bars) and alkylated galectin (blue bars), in different concentrations of aptamer (0 µM, 10 µM, 35 µM, 40 µM). The lectin concentration was 5 µM in all measures.

Initially, it should be noted that all 41 sequences are functional and have great interaction and inhibition effects, as they were obtained from the SELEX process. However, in an initial scan, the 4 main sequences (SEQ ID NO. 4, SEQ ID NO 9, SEQ ID NO 10 and SEQ ID NO 12) showed a greater variation in the denaturation temperature (Tm) of hGal1 and a better effect on the inhibition of hemagglutination induced by galectin, therefore, they were chosen for in vitro tests. The Tm scan and hemagglutination inhibition data are shown in FIGS. 15, 16 and 17. Those figures refer to the SEQ ID NO 4 and SEQ ID NO 9, but the results are similar for the SEQ ID NO 10 and SEQ ID NO 12.

From the sequences above it was possible to group said sequences in order to assign a Markush formula to each group:

Group 1 selected from SEQ ID NOs 1 to 20, where said aptamer has the following formula (1) SEQ ID NO 46:

AGCTGACACAGCAGGTTGGTGCXan$_1$Xan$_2$Xan$_3$Xan$_4$Xan$_5$Xan$_6$Xan$_7$

Xan$_8$Xan$_9$Xan$_{10}$Xan$_{11}$Xan$_{12}$Xan$_{13}$Xan$_{14}$Xan$_{15}$Xan$_{16}$Xan$_{17}$Xan$_{18}$

Xan$_{19}$Xan$_{20}$Xan$_{21}$Xan$_{22}$Xan$_{23}$Xan$_{24}$Xan$_{25}$Xan$_{26}$Xan$_{27}$Xan$_{28}$Xan$_{29}$

Xan$_{30}$Xan$_{31}$Xan$_{32}$Xan$_{33}$Xan$_{34}$Xan$_{35}$Xan$_{36}$Xan$_{37}$Xan$_{38}$Xan$_{39}$Xan$_{40}$

Xan$_{41}$Xan$_{42}$Xan$_{43}$Xan$_{44}$Xan$_{45}$Xan$_{46}$Xan$_{47}$Xan$_{48}$Xan$_{49}$Xan$_{50}$Xan$_{51}$

Xan$_{52}$CCGAGTCGAGCAATCTCGAAAT wherein:
Xan$_1$, Xan$_6$, Xan$_7$, Xan$_8$, Xan$_9$, Xan$_{10}$, Xan$_{11}$, Xan$_{12}$, Xan$_{16}$, Xan$_{17}$, Xan$_{18}$, Xan$_{26}$, Xan$_{28}$, Xan$_{32}$, Xan$_{34}$, Xan$_{35}$, Xan$_{36}$, Xan$_{40}$, Xan$_{41}$, Xan$_{42}$, Xan$_{48}$, Xan$_{49}$, Xan$_{50}$, Xan$_{51}$ and Xan$_{52}$ are A, T, C, G or absent;

Xan$_2$, Xan$_3$, Xan$_4$, Xan$_5$, Xan$_{13}$, Xan$_{14}$, Xan$_{15}$, Xan$_{19}$, Xan$_{20}$, Xan$_{21}$, Xan$_{22}$, Xan$_{23}$, Xan$_{24}$, Xan$_{25}$, Xan$_{27}$, Xan$_{30}$, Xan$_{31}$, Xan$_{33}$, Xan$_{37}$, Xan$_{38}$, Xan$_{39}$, Xan$_{43}$, Xan$_{44}$ and Xan$_{45}$ are A, T, C, G;

Xan$_{46}$ is A, T, C or absent; and
Xan$_{47}$ is T, C, G or absent.

Group 2 selected from SEQ ID NOs 4, 9, 10 and 12, where said aptamer has the following formula (2) SEQ ID NO 47:

AGCTGACACAGCAGGTTGGTGCXan$_1$Xan$_2$Xan$_3$Xan$_4$Xan$_5$AXan$_6$Xan$_7$

Xan$_8$Xan$_9$Xan$_{10}$Xan$_{11}$Xan$_{12}$Xan$_{13}$Xan$_{14}$Xan$_{15}$Xan$_{16}$Xan$_{17}$Xan$_{18}$

Xan$_{19}$Xan$_{20}$Xan$_{21}$Xan$_{22}$Xan$_{23}$Xan$_{24}$Xan$_{25}$Xan$_{26}$Xan$_{27}$Xan$_{28}$Xan$_{29}$

Xan$_{30}$Xan$_{31}$Xan$_{32}$Xan$_{33}$Xan$_{34}$Xan$_{35}$Xan$_{36}$Xan$_{37}$Xan$_{38}$Xan$_{39}$Xan$_{40}$

Xan$_{41}$Xan$_{42}$Xan$_{43}$Xan$_{44}$AXan$_{45}$Xan$_{46}$Xan$_{47}$Xan$_{48}$CCGAGTCGAGCAA

TCTCGAAAT wherein:
Xan$_1$ and Xan$_{45}$ are C or is absent;
Xan$_2$, Xan$_{14}$, Xan$_{17}$, Xan$_{27}$, Xan$_{30}$, Xan$_{34}$, Xan$_{36}$ and Xan$_{48}$ are A, C or G;
Xan$_3$, Xan$_4$, Xan$_9$, Xan$_{10}$, Xan$_{16}$, Xan$_{25}$, Xan$_{33}$ and Xan$_{40}$ are A or C;
Xan$_5$, Xan$_7$, Xan$_{20}$, Xan$_{22}$, Xan$_{32}$, Xan$_{37}$ and Xan$_{38}$ are A, C or T;
Xan$_6$, Xan$_8$, Xan$_{11}$, Xan$_{29}$, Xan$_{41}$ and Xan$_{47}$ are A or G;
Xan$_{12}$, Xan$_{24}$, Xan$_{31}$ and Xan$_{46}$ are A, G or T;
Xan$_{15}$, Xan$_{21}$, Xan$_{23}$ and Xan$_{35}$ are C or G;
Xan$_{18}$ and Xan$_{43}$ are G or T;

Xan$_{19}$, Xan$_{39}$ and Xan$_{44}$ are A or T;
Xan$_{26}$ and Xan$_{42}$ are C, G or T;
Xan$_{28}$ is C or T;
Group 3 selected from SEQ ID NOs 21 to 31, where said aptamer has the following formula (3) SEQ ID NO 48:

ATTTCGAGATTGCTCGACTCGGXan$_1$Xan$_2$Xan$_3$Xan$_4$Xan$_5$Xan$_6$Xan$_7$

Xan$_8$Xan$_9$Xan$_{10}$Xan$_{11}$Xan$_{12}$Xan$_{13}$Xan$_{14}$Xan$_{15}$Xan$_{16}$Xan$_{17}$Xan$_{18}$

Xan$_{19}$Xan$_{20}$Xan$_{21}$Xan$_{22}$Xan$_{23}$Xan$_{24}$Xan$_{25}$Xan$_{26}$Xan$_{27}$Xan$_{28}$Xan$_{29}$

Xan$_{30}$Xan$_{31}$Xan$_{32}$Xan$_{33}$Xan$_{34}$Xan$_{35}$Xan$_{36}$Xan$_{37}$Xan$_{38}$Xan$_{39}$Xan$_{40}$

Xan$_{41}$Xan$_{42}$Xan$_{43}$Xan$_{44}$Xan$_{45}$Xan$_{46}$Xan$_{47}$Xan$_{48}$Xan$_{49}$Xan$_{50}$Xan$_{51}$

GCACCAACCTGCTGTGTCAGCT wherein:

Xan$_1$, Xan$_2$, Xan$_5$, Xan$_6$, Xan$_{15}$, Xan$_{22}$, Xan$_{23}$, Xan$_{34}$, Xan$_{35}$, Xan$_{49}$, Xan$_{50}$ and Xan$_{51}$ are A, T, C, G or absent;

Xan$_3$, Xan$_4$, Xan$_7$, Xan$_8$, Xan$_9$, Xan$_{10}$, Xan$_{11}$, Xan$_{12}$, Xan$_{13}$, Xan$_{14}$, Xan$_{16}$, Xan$_{17}$, Xan$_{18}$, Xan$_{19}$, Xan$_{20}$, Xan$_{24}$, Xan$_{25}$, Xan$_{26}$, Xan$_{27}$, Xan$_{28}$, Xan$_{29}$, Xan$_{30}$, Xan$_{31}$, Xan$_{32}$, Xan$_{33}$, Xan$_{36}$, Xan$_{37}$, Xan$_{38}$, Xan$_{39}$, Xan$_{40}$, Xan$_{41}$, Xan$_{42}$, Xan$_{43}$, Xan$_{44}$, Xan$_{45}$, Xan$_{46}$ and Xan$_{48}$ are A, T, C, G;

Xan$_{21}$ is C, G or T; and
Xan$_{47}$ is A, G or T.

It is important to note that any new nucleotide sequence, chemically modified or not (aptamer), which has at least 80% or more of its sequence similar to one of the sequences of the 41 aptamers or their tridimensional structure disclosed in the present application will be considered analogous to the aptamers described herein.

In order to make it possible to select and identify the aptamers previously described, the following procedures were performed:

Preparation of Purified hGal-1

The purification of human recombinant galectin-1 was done as previously described using transformed *E. coli* strain (M-15) containing the plasmid expressing human galectin-1 and affinity chromatography on lactosyl-Sepharose.

SELEX

Oligonucleotides were purchased as lyophilized oligonucleotide. Before use, distilled water dissolved ssDNA library and aptamers were heated at 95° C. for 2 min and immediately cooled on ice. All the other reagents used for chemical and biological characterization were of analytical grade. The library and primer details are as follows: library: 5'-AGCTGACACAGCAGGTTGGTGC N49 CCGAGTCGAGCAATCTCGAAAT-3' (SEQ ID NO: 43); forward: 5'AGCTGACACAGCAGGTTGGTGC3' (SEQ ID NO: 44); reverse: 5'ATTTCGAGATTGCTCGACTCGG3' (SEQ ID NO: 45). Libraries were amplified by PCR before selection.

Polypropylene microtubes (0.2 mL) were coated and blocked with 2 mg/mL hGal1 in coating buffer (20 mM HEPES, pH 7.4, 200 µL) overnight at 4° C. Previously selections steps, microtubes were washed 3 times with coating buffer. In the first round of selection, 1 nmol of ssDNA library (theoretically 1014 different oligonucleotides) was distributed in hGal1-coated microtubes and incubated at room temperature for 2 h. After incubation, the supernatant was discarded and the microtubes were washed 3 times with 200 µL of washing buffer. To elute the bound ssDNA, 100 µL of ddH2O was added to a microtube and placed in a dry bath heat block at a temperature of 95° C. for 15 min. The supernatant was collected and used as the template for PCR amplification of hGal1 bound ssDNA. After the fourth selection round, the collected aptamers were amplified by PCR. The dsDNA product was resolved on 3% agarose gel and the corresponding bands on the gel were purified, cloned, and sequenced.

Selection of DNA Aptamers

A ssDNA library comprising around $5 \times 10^{14}$ molecules was applied in hGal1 DNA aptamers selection. Following 4 rounds of selection, sixteen different sequences from twenty-one clones were collected. The classical SELEX process involves multiple rounds of selection and amplification. Here, a modified SELEX selection was performed, and all selection and amplification steps took place in one single vial, without using a conventional blocking step, as described above. Briefly, immobilized galectin was incubated with the aptamer library. Thereafter, unbound aptamers were wiped out and PCR reagents were added to the microtube, and aptamers bound to the lectin were amplified. The protein denaturation caused by the high temperature through the first PCR cycle releases the bound aptamers and allowed for their amplification in successive PCR cycles. These aptamers were cloned and sequenced; 41 sequences were obtained. None of the sequences were identical and some sequences were truncated, hence they were not further analyzed. Aptamers were selected for further analysis if they induced a thermoshift exhibited ΔTm (in TSA experiments) higher than 2.0° C. One of the oligonucleotides, named SEQ ID NO.: 4 showed the best performance via TSA screening and therefore was analyzed in more detail.

SEQ ID NO.: 4 Induces Thermostability Decreasing of Native hGal1

In an attempt to screen among the selected aptamers that better interact with hGal1, differential scanning fluorimetry (Termofluor) was used to characterize their binding to its target. Among all the selected aptamers, SEQ ID NO.: 4 seemed to have a more intense effect on hGal1 thermoshift and so was chosen for further analysis. The selected aptamer had its interaction evaluated with native and alkylated galectin-1. The reference curve for each protein showed a sigmoidal profile with Tm values of 57.8±0.7° C. for native galectin-1 and 64.68±0.04° C. for alkylated galectin-1. The respective thermal displacements were evaluated as a function of an increasing concentration of SEQ ID NO.: 4 (FIG. 1). The inventors observed that for the native protein there is a marked decrease in Tm for SEQ ID NO.: 4, but not in a dose-response manner. On the other hand, the temperature variation for the alkylated protein was not significant, which implies that the alkylation process protects the protein from the destabilizing effect of the aptamer. This suggests that the aptamer and protein interaction occur mainly in the convex region of the lectin CRD, where the major electronic and steric modifications occur after the addition of acetamide groups (alkylation). This result together with the hemagglutination data indicates that the aptamer may interact at the dimerization interface causing a destabilization of the structure which leads to a decrease in Tm.

Thermofluor Assays (TSA)

Thermofluor experiments were performed on an Mx3005 RT-PCR (Agilent Technologies) using the SYPRO® Orange dye (492/610 nm) (Invitrogen) as fluorescent probe. The purified (native and alkylated) protein samples were incubated for 30 min with increasing concentration of the molecules of interest, centrifuged, and submitted to the thermal denaturation assay, totalizing four distinct experiments. In a 96-well plate (Agilent Technologies) 20 µl of the reaction containing 5 µM of each protein in buffer PBS 1× and 5× SYPRO® Orange were heated from 25° C. to 95° C. at a rate of 1° C./min. The experimental result was processed as in the protocol previously described and the melting temperature was obtained using GraphPad Prism software (www.graphpad.com).

Fluorescence Quenching

Fluorescence measurements were taken by a spectrofluorimeter HITACHI F-4500, the spectra were collected by excitation and emission at a rate of 240 nm per min, using a 5 nm slit widths and recorded at room temperature. A total of 5 µM hGal1 solution was incubated for 10 hours with aptamer aliquots as quencher, from 0 to 7.2 µM, in PBS 1× buffer. The spectra were obtained between 300-450 nm after excitation at 295 nm and all buffer contributions were corrected for measurements. As previously described, the log of fluorescence quenching was evaluated by plotting it versus log of aptamer concentration. The Stern-Volmer equation was used to estimate the number of interacting sites (n) and the apparent kD.

The hGal1/SEQ ID NO. 4 Interaction Promotes Fluorescence Quenching

Figure 1C:
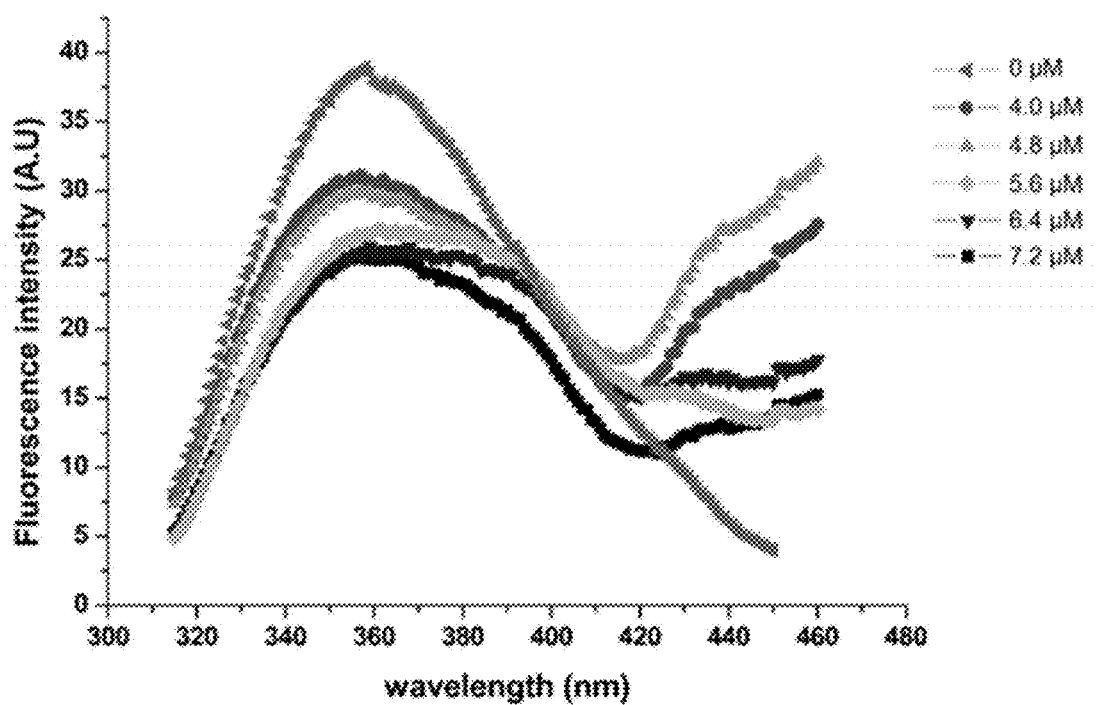
Figure 1D:
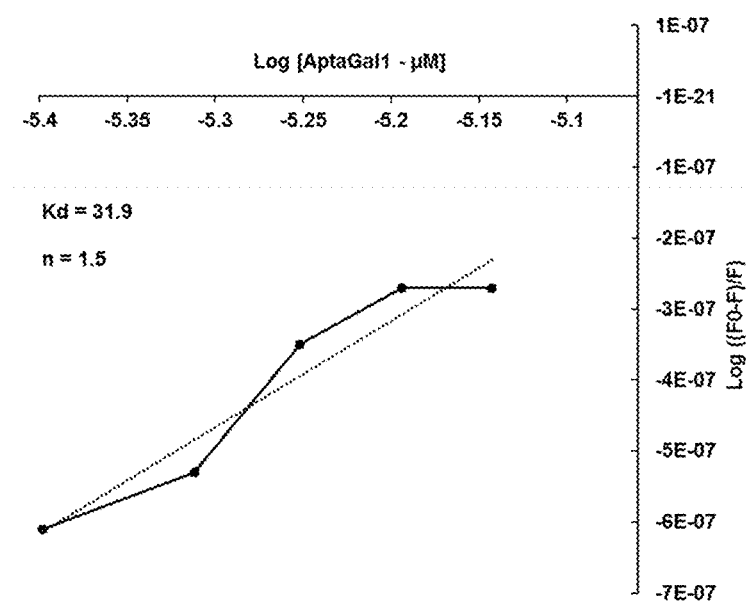

Human galectin-1 tryptophan residue has an emission peak at 348 nm after 280 nm exited. SEQ ID NO.: 4 promotes changes the fluorescence spectrum of Trp68, which is the sole Trp in the subunit of hGal1 and is one of the residues constituting its CRD. Upon the aptamer addition, fluorescence emission decreased (FIG. 1C). The fluorescence quenching log versus aptamer concentration log measurements was plotted and it was fitted with Stern-volmer equation. The best fit established apparent dissociation constant of approximately 31.9 nM and a binding site of 1.5 (FIG. 1D).

Hemagglutination Inhibition Assay

Hemagglutination assay was adopted to assess the capacity of SEQ ID NO.: 4 in inhibiting the lectin cross-linking aggregation of red blood cells (RBC), as previously described. Briefly, using a 96-well microplates appropriate amounts of 5 µM hGal1 were blended with 50 µL of aptamer in an increasing concentrations manner (0-40 µM) in PBS 1× buffer (pH 7.4). Following, 50 µL of 3% purified type B+ RBC in PBS. After 2 h of room temperature incubation, the plate was photographed and the hemagglutination area was estimated by area calculator Sketchandcalc™ and the results were expressed as relative agglutination.

SEQ ID NO. 4 Inhibits hGal1-Induced Hemagglutination

Figure 2A:
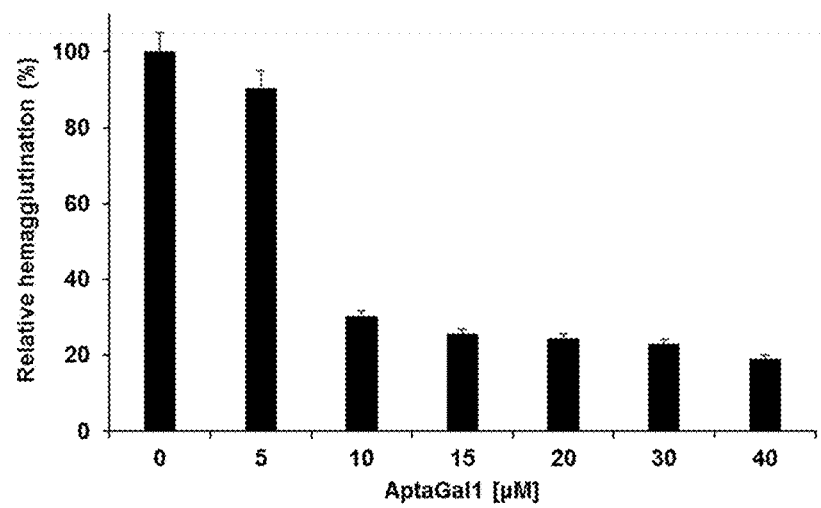
FIG. 2A represents the erythrocytes that were incubated with 5 μM of rhgal in a presence of 0, 5, 10, 15, 20, 30 and 40 μM of AptaGal1. From 10 to 40 μM of AptaGal1, Gal1 lost the ability to form erythrocyte lattice and this effect occurs in a dose-dependent manner. The positive hemagglutination control is represented by 0 μM of SEQ ID NO.: 4.
Figure 2B:
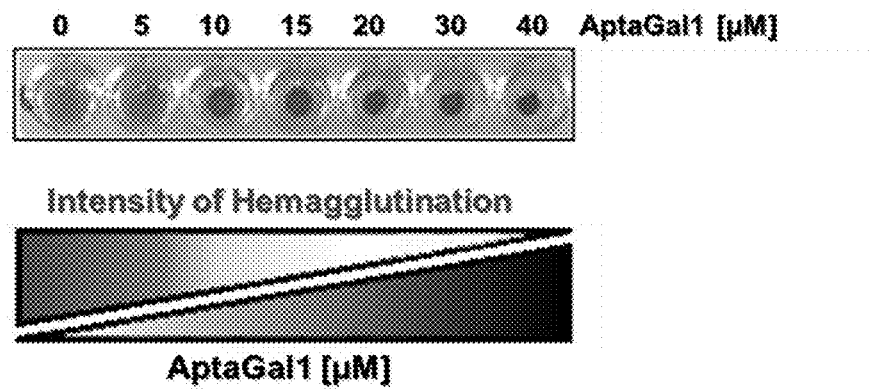
FIG. 2B shows the data expressed as a relative hemagglutination (%) in relation to the positive control.
Figure 3A:
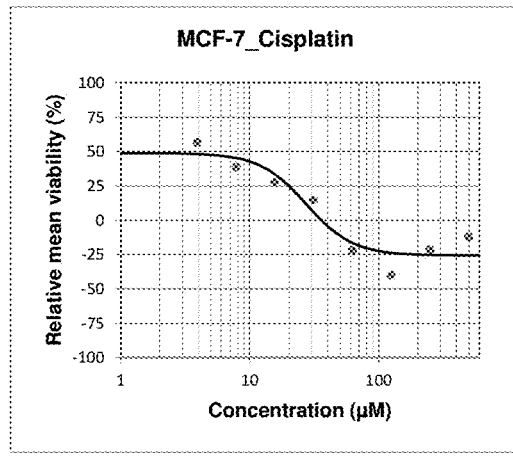
FIG. 3 shows a 4-parameter logistic regression to define the IC50 values (concentration to inhibit 50% of cell growth). TGI (concentration for total cell growth inhibition) and LC50 (concentration for 50% cell death) of the reference item Cisplatin against tumor lines MCF-7 (A). DU-145 (B). A-375 (C). HT-29 (D). HCT 116 (E). SK-BR-3 (F). OVCAR-3 (G) and normal human NHF fibroblasts (H).
Figure 3B:
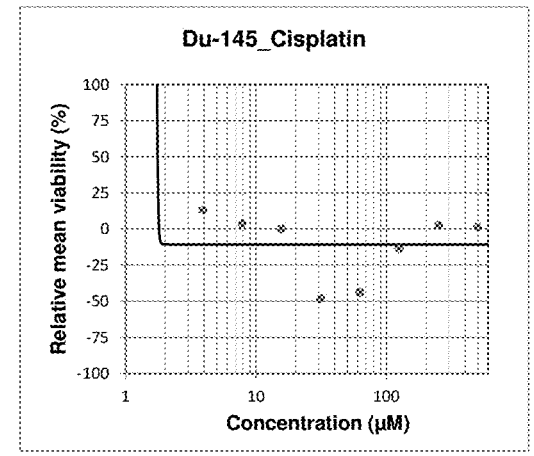
Figure 3C:
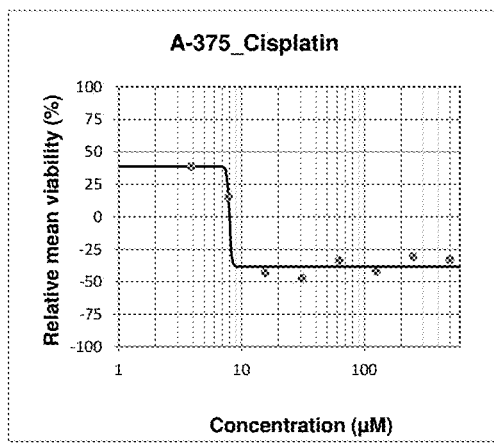
Figure 3D:
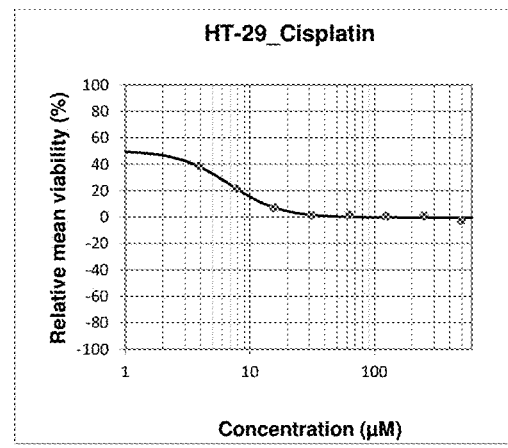
Figure 3E:
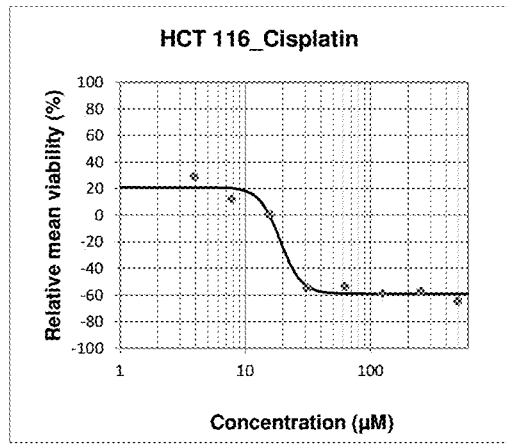
Figure 3F:
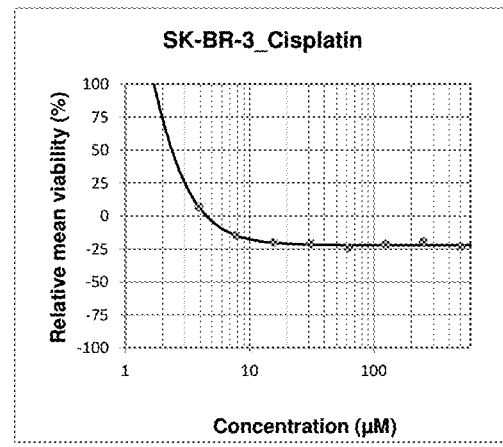
Figure 3G:
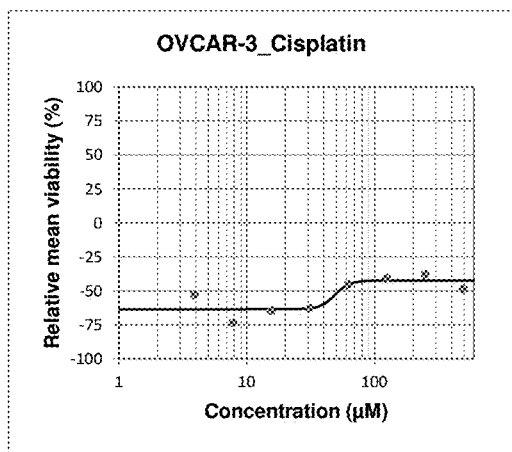
Figure 3H:
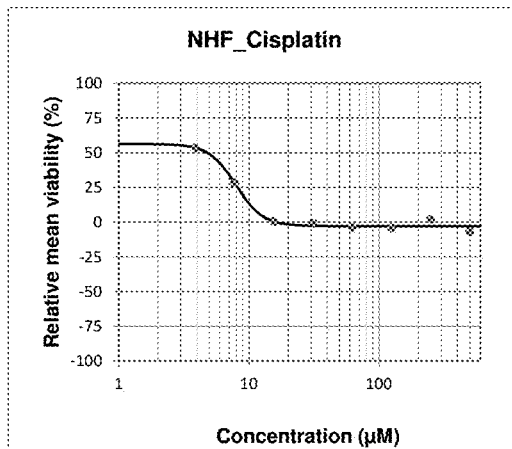
Figure 4A:
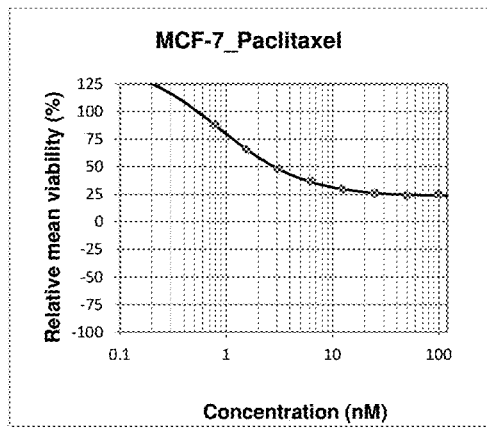
FIG. 4 shows a 4-parameter logistic regression to define the IC50 values (concentration for 50% inhibition of cell growth). TGI (concentration for total cell growth inhibition) and LC50 (concentration for 50% cell death) of the reference item Paclitaxel against tumor lines MCF-7 (A). DU-145 (B). A-375 (C). HT-29 (D). HCT 116 (E). SK-BR-3 (F). OVCAR-3 (G) and normal human NHF fibroblasts (H).
Figure 4B:
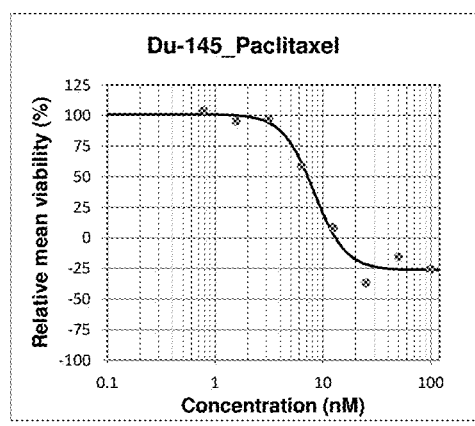
Figure 4C:
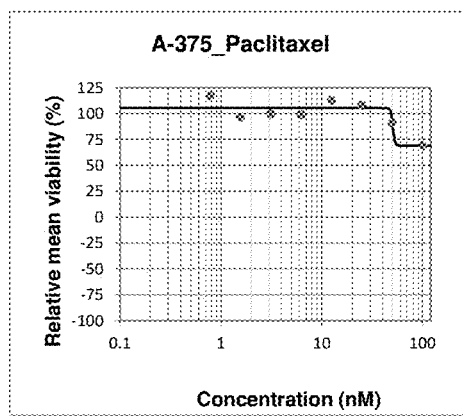
Figure 4D:
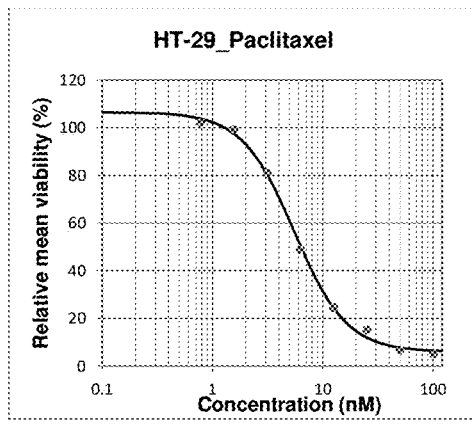
Figure 4E:
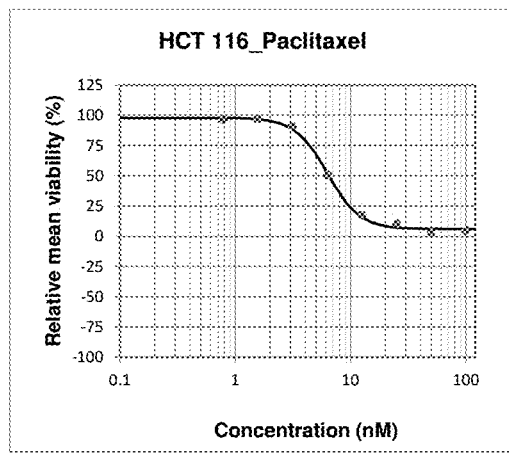
Figure 4F:
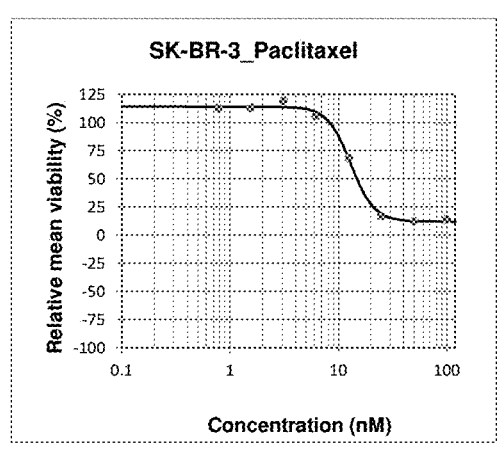
Figure 4G:
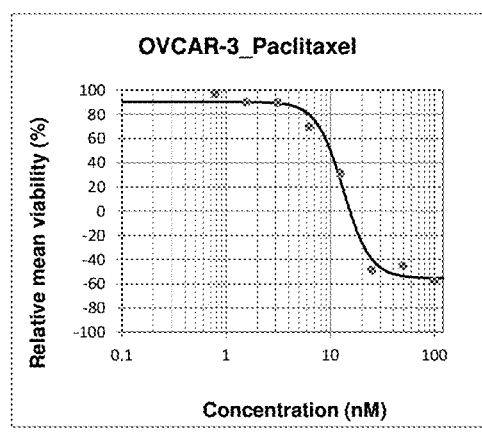
Figure 4H:
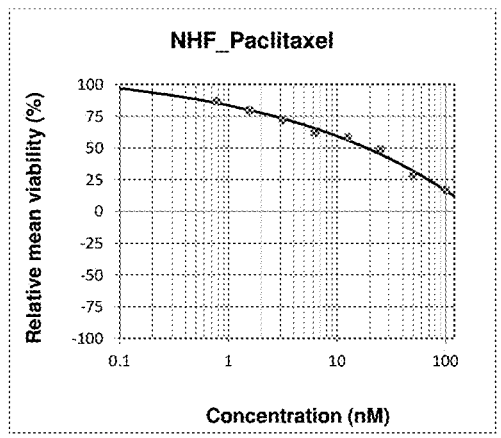
Figure 5A:
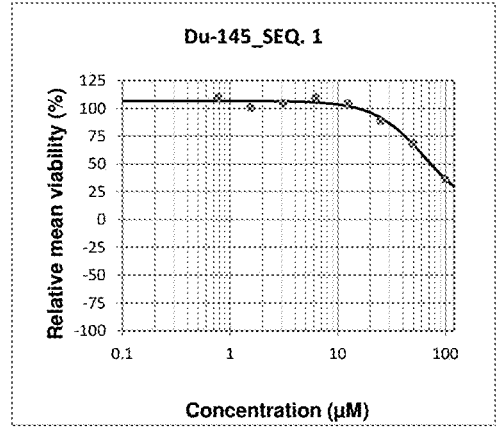
FIG. 5 illustrates a 4-parameter logistic regression to define the IC50 values (concentration for 50% inhibition of cell growth). TGI (concentration for total cell growth inhibition) and LC50 (concentration for 50% cell death) of the test items against the DU-145 tumor line.
Figure 5B:
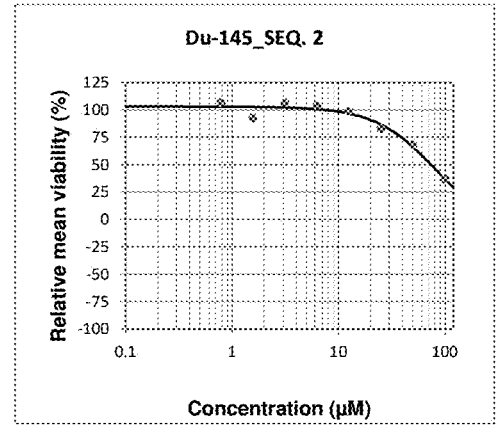
Figure 5C:
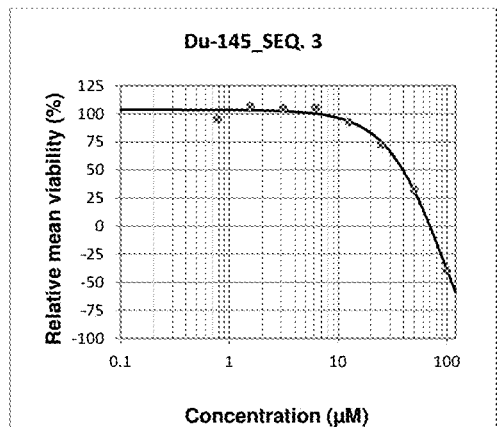
Figure 5D:
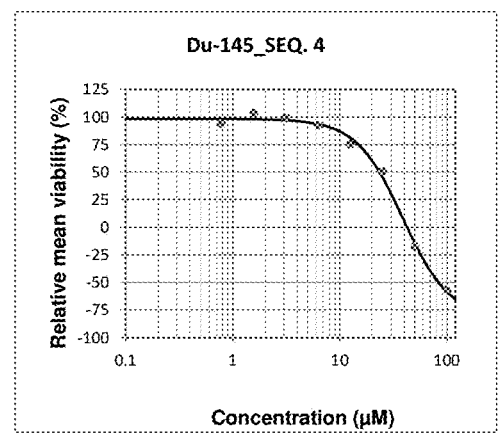
Figure 5E:
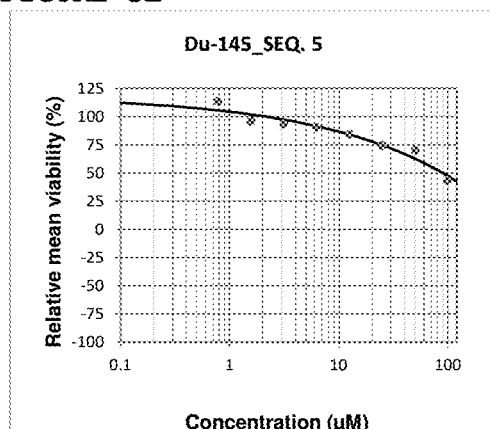
Figure 6A:
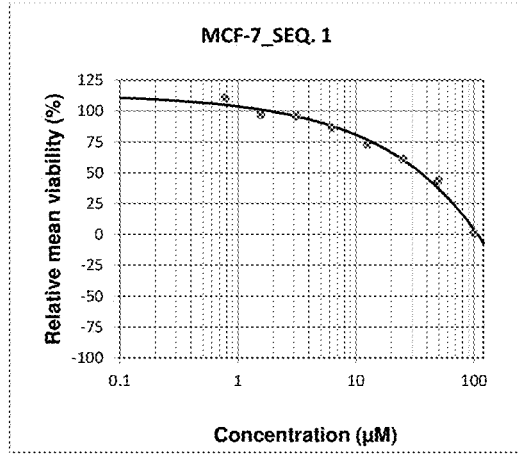
FIG. 6 shows a 4-parameter logistic regression for defining the IC50 values (concentration for 50% inhibition of cell growth). TGI (concentration for total cell growth inhibition) and LC50 (concentration for 50% cell death) of the test items against the MCF-7 tumor line.
Figure 6B:
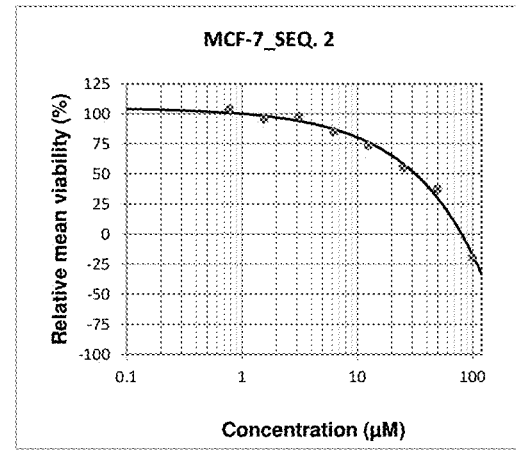
Figure 6C:
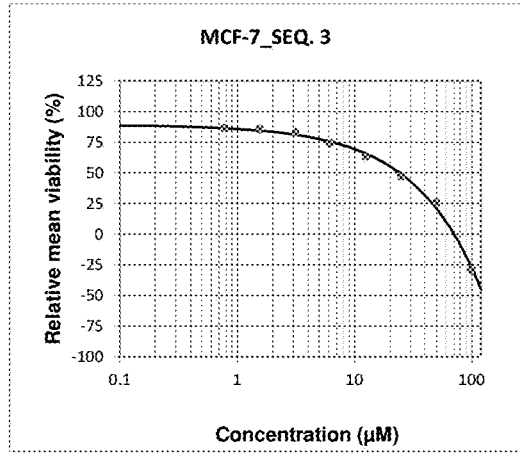
Figure 6D:
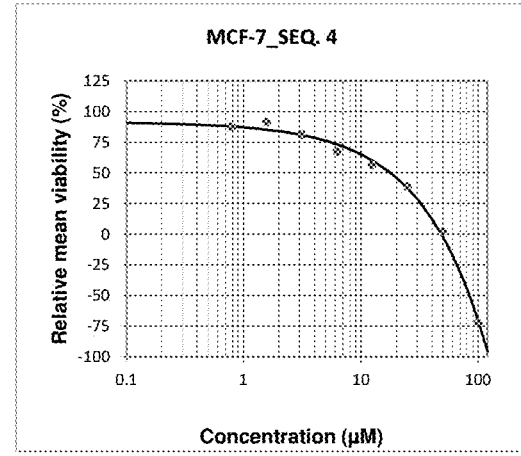
Figure 6E:
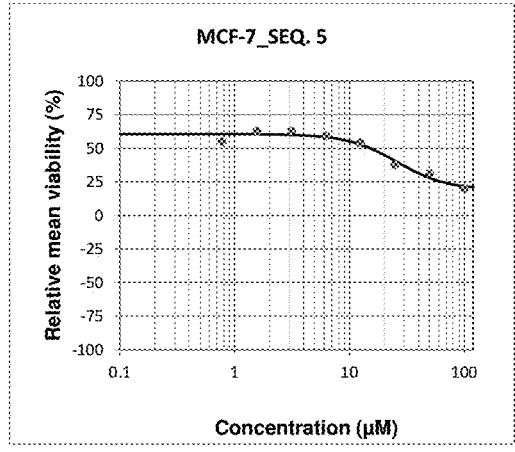
Figure 7A:
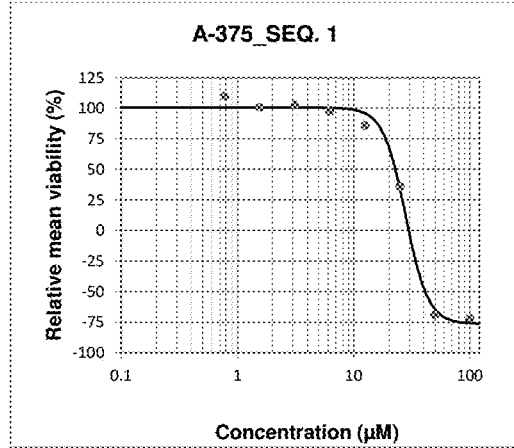
FIG. 7 shows a logistic regression of 4 parameters to define the IC 50 values (concentration for inhibition of 50% of cell growth). TGI (concentration for total cell growth inhibition) and LC50 (concentration for 50% cell death) of the test items against the tumor line A-375.
Figure 7B:
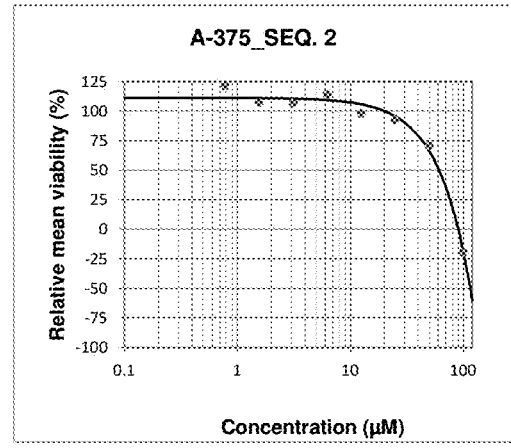
Figure 7C:
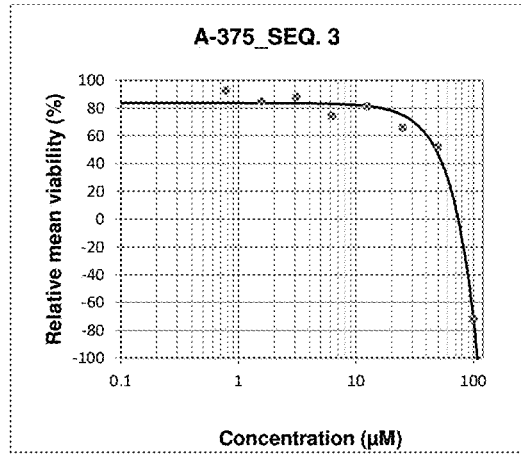
Figure 7D:
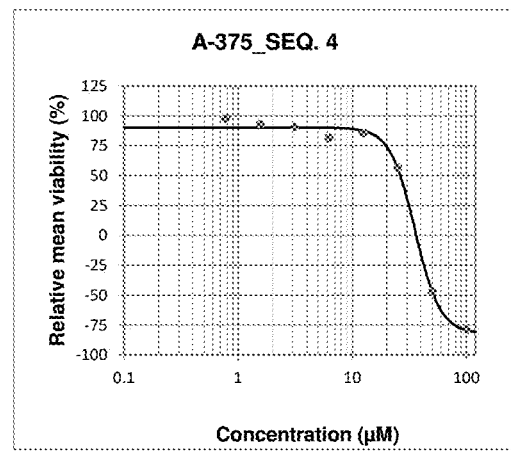
Figure 7E:
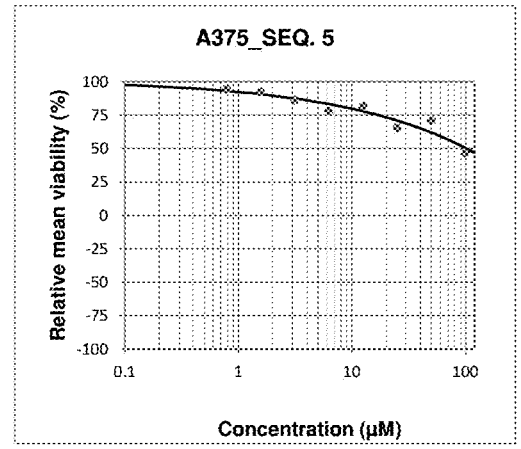
Figure 8A:
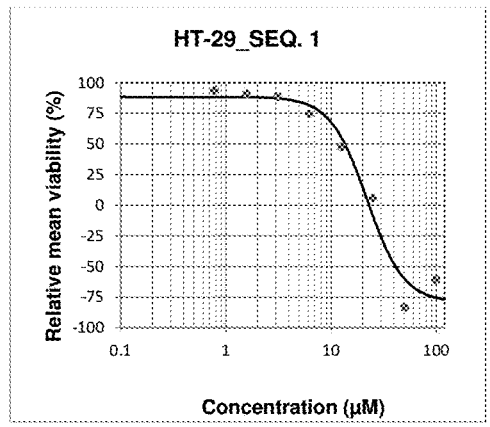
FIG. 8 shows a 4-parameter logistic regression for defining IC50 values (concentration for inhibiting 50% cell growth). TGI (concentration for total cell growth inhibition) and LC50 (concentration for 50% cell death) of the test items against the HT-29 tumor line.
Figure 8B:
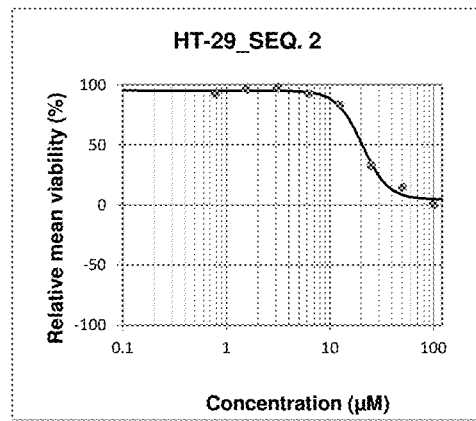
Figure 8C:
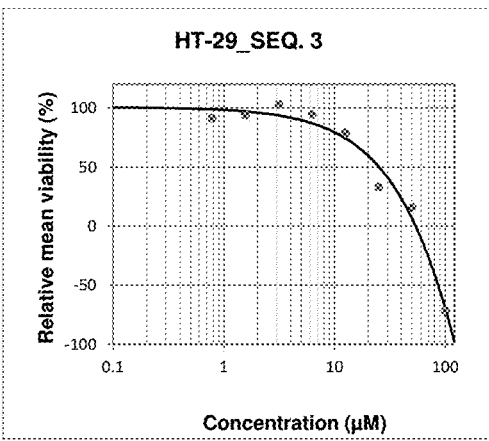
Figure 8D:
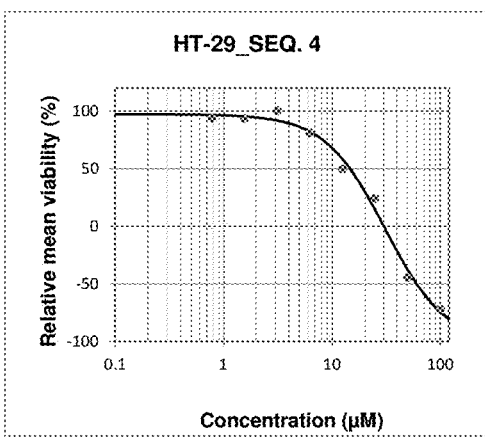
Figure 8E:
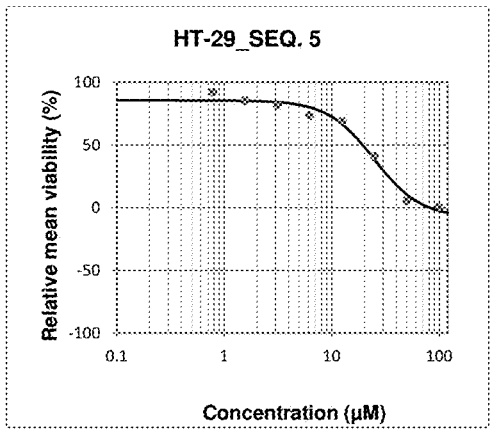
Figure 9A:
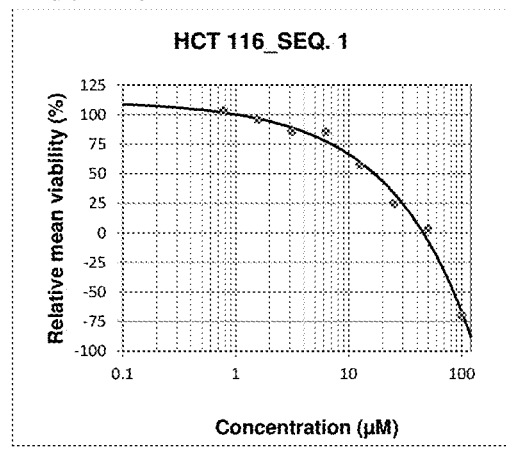
FIG. 9 shows a 4-parameter logistic regression to define the IC50 values (concentration for 50% inhibition of cell growth), TGI (concentration for total inhibition of cell growth) and LC50 (concentration for 50% cell death) of test items against the HCT 116 tumor line.
Figure 9B:
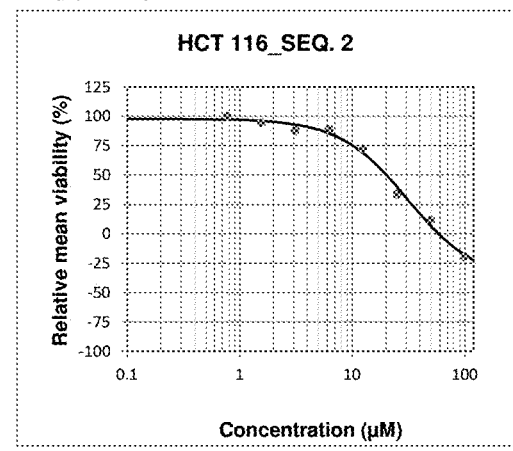
Figure 9C:
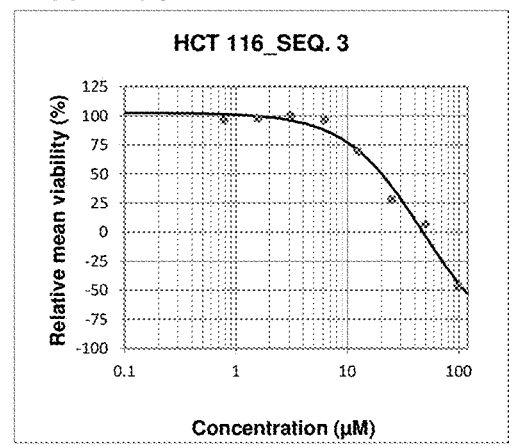
Figure 9D:
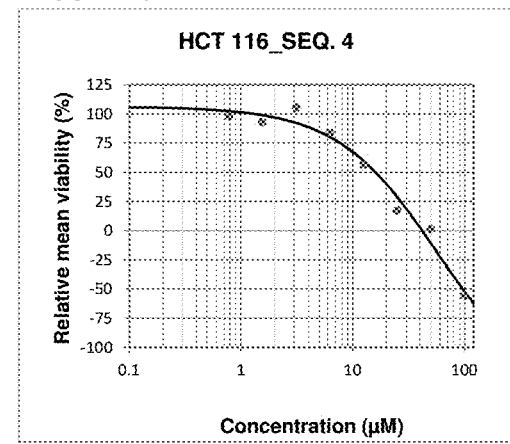
Figure 9E:
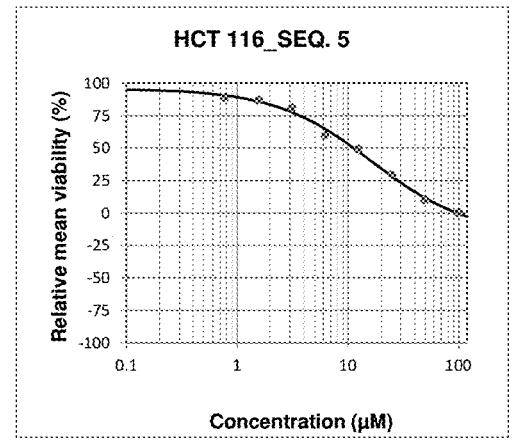
Figure 10A:
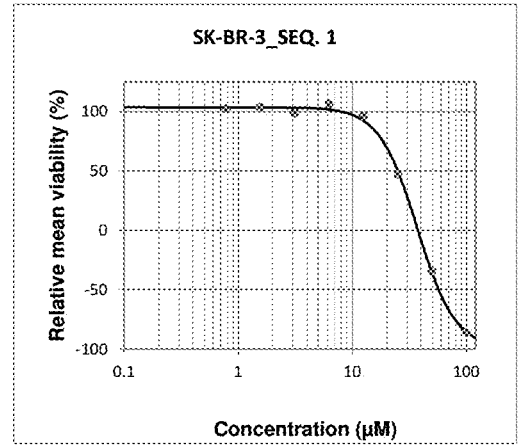
FIG. 10 shows a 4-parameter logistic regression to define the IC50 values (concentration for 50% cell growth inhibition), TGI (concentration for total cell growth inhibition) and LC50 (concentration for 50% cell death) of test items against the SK-BR-3 tumor line.
Figure 10B:
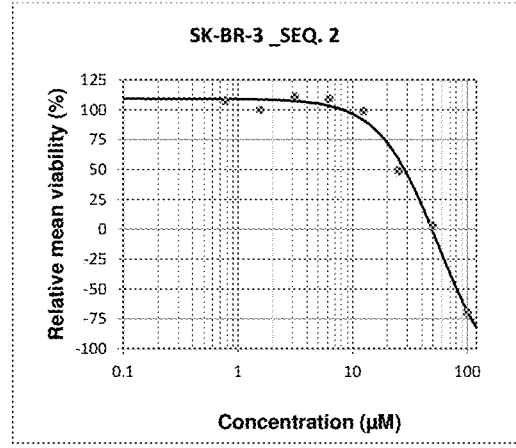
Figure 10C:
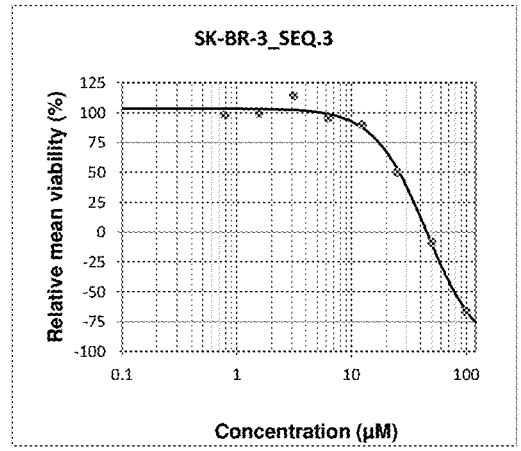
Figure 10D:
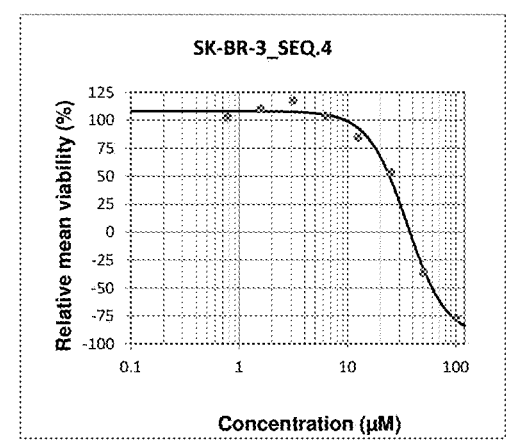
Figure 10E:
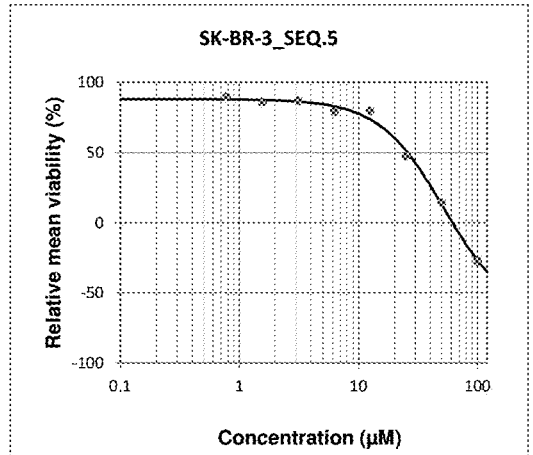
Figure 11A:
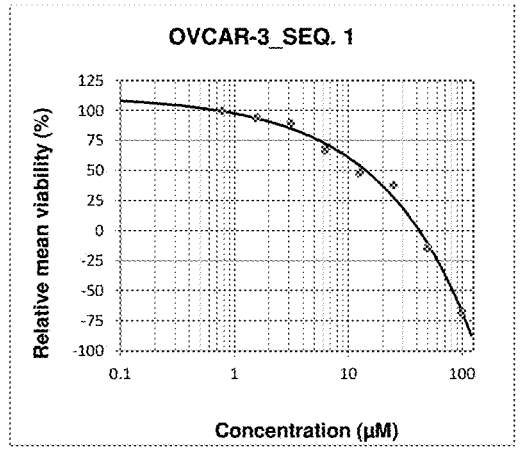
FIG. 11 shows a 4-parameter logistic regression to define the IC50 values (concentration for inhibition of 50% cell growth), TGI (concentration for total inhibition of cell growth) and LC50 (concentration for 50% cell death) of test items against the tumor line OVCAR-3.
Figure 11B:
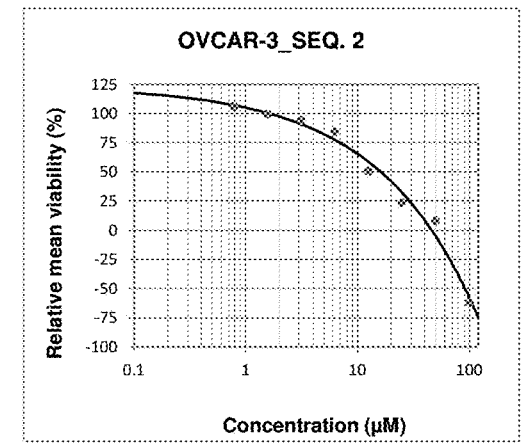
Figure 11C:
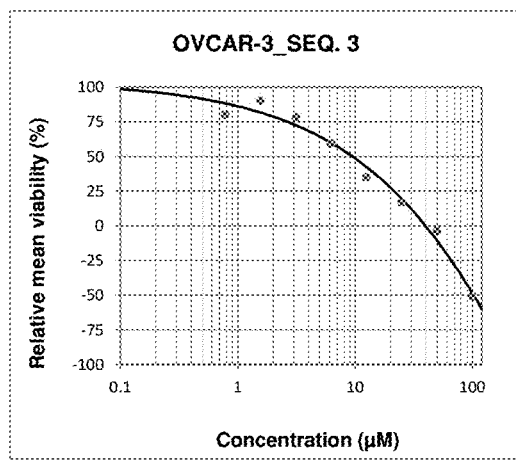
Figure 11D:
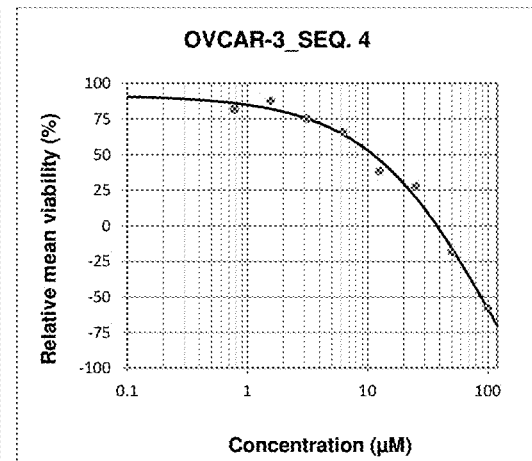
Figure 11E:
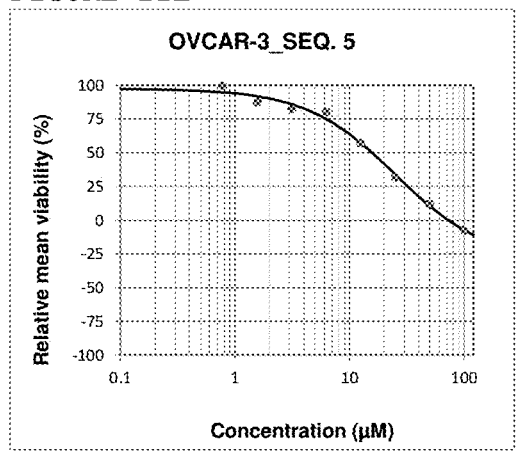
Figure 12A:
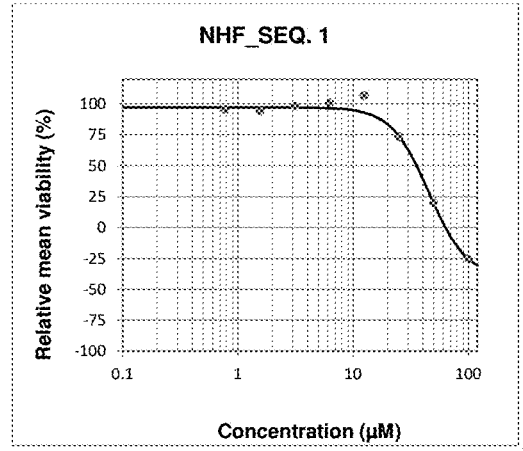
FIG. 12 shows a 4-parameter logistic regression to define the IC50 values (concentration for 50% inhibition of cell growth), TGI (concentration for total inhibition of cell growth) and LC50 (concentration for 50% cell death) of test items against the NHF cell line.
Figure 12B:
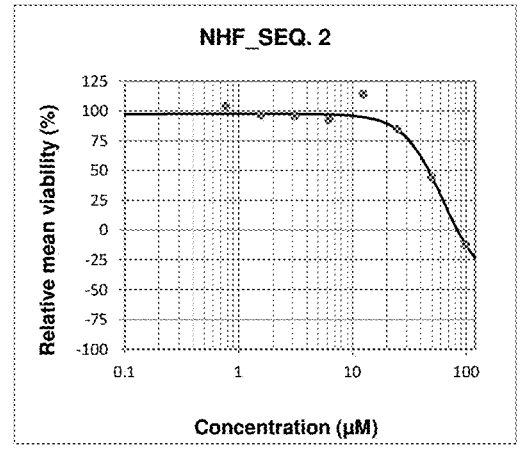
Figure 12C:
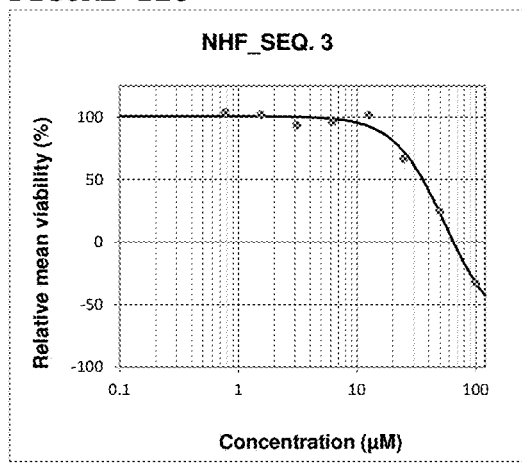
Figure 12D:
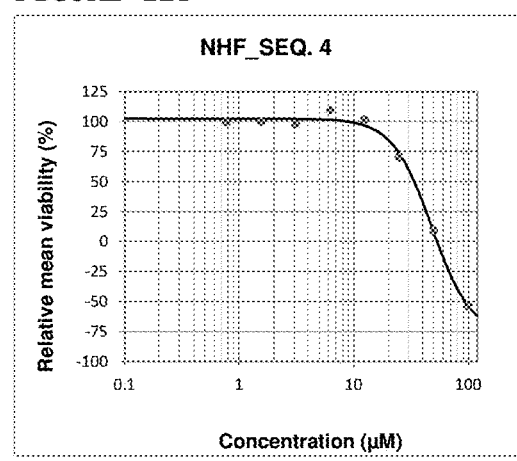
Figure 12E:
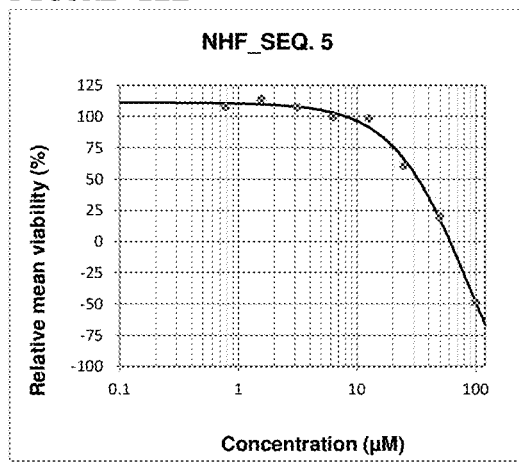

Later, in vitro functional properties of SEQ ID NO.: 4 were evaluated. The aptamer potential of interfering with the RBC agglutination mediated by hGal1 was assessed (FIG. 2A). Because hemagglutination occurs by the cross-linking among lectin to the glycans of the cell surface, reducing in agglutination levels by SEQ ID NO.: 4 addition might be justified by diminished glycan binding caused by the aptamer interaction with hGal1. FIG. 2A illustrates the extensive network by the hGal1-RBC cross-link formation, as expected in the aptamer absence. SEQ ID NO.: 4 was capable to inhibit the lattice formation, and upon addition of an increasing concentration, it became clear that hemagglutination is extremely reduced, indicating that the addition of 10 µM of SEQ ID NO.: 4 has approximately 75% of inhibition effect over RBC agglutination (FIG. 2B). These data indicate that SEQ ID NO.: 4 can somehow block hGal1 function, thereby reducing multivalent interactions of this lectin on the cell surface.

Cytotoxicity Assay

The antiproliferative effects of aptamers were in vitro evaluated on seven cell lines of solid human tumors, and the 50% growth inhibitory concentrations (IC50) ranged from 9.45 to 74.02 µM (Table 1 to 5). On average, higher concentrations of OTX008 and anginex, well-known galectin-1 inhibitors, are needed to obtain antiproliferative effects equivalent to those of aptamers (>100 uM IC50 in most assessed cell lines). For the analysis of cell proliferation, the non-clonogenic method of sulforodamine B (SRB) was used, a protein dye that binds to the basic amino acid residues of cell proteins that were viable at the time of the fixation process. Therefore, the greater the amount of SRB bound per compartment, the less the antiproliferative activity of the item under study.

The XLSTAT software was used to determine the IC50, TGI and LC50 values using the four-parameter logistic curve equation.

Table 1 and FIG. 3 show the results of the reference items Cisplatin and Paclitaxel evaluated in 8 concentrations against the human tumor lines SK-BR-3, MCF-7, DU-145, OVCAR-3, HT-29, HCT 116, A-375 and normal human NHF fibroblasts. As can be observed, Table 1 shows that both cisplatin and paclitaxel presented a very low IC50 and TGI 50 values for all tumor lines evaluated. These data that are accordingly with the literature, and corroborate their applications in oncology therapies, as well as their use as reference drugs (positive control) in the present invention.

The results for the test items evaluated against the tumor lines Du-145 and MCF-7 are described in Table 2. The graphs represented in FIGS. 4 and 5 correspond to the logistic regression of 4 parameters for calculating the IC50 parameters. TGI and LC50 of the test items when evaluated in the DU-145 and MCF-7 lines respectively.

Tables 2, 3, 4 and 5 show that all aptamers evaluated (SEQ. ID NO 4, 9, 10 and 12) in the relative cell viability assay against tumor lines (DU-145, MCF-7, A-375, HT-29, HCT-116, SKBR-3, and OVCAR-3) presented IC50 values much lower than the reference galectin-1 inhibitors previously described, proving their high and improved efficiencies concerning antiproliferative activity in tumor cells, as well as a notorious potential for therapeutic application.

It is also observed that the negative control did not show lethality for the tumor cell lines within the concentrations range evaluated in the assay, as well as IC50 or TGI50 values, always much higher than those presented by aptamers, especially SEQ. ID NO 10 and 12. These data support the non-specificity of the molecule concerning the observed antiproliferative effects, as expected.

It is also significant to observe that the aptamer SEQ. ID NO 10 presented IC50 values below 25 µM when tested against all tumor cell lines assessed. This value is much lower than that of any other galectin-1 inhibitor already described. These data make clear of its exceptional antitumor effect, as well as its high potential for application in cancer therapy.

TABLE 1

Results of relative viability and IC50, ITG and LC50 values of the reference items Cisplatin and Paclitaxel.

| Positive Control Item | Concentration | Relative cell viability (%) | | | | | | | |
|---|---|---|---|---|---|---|---|---|---|
| | | MCF-7 | DU-145 | A-375 | HT-29 | HCT 116 | SK-BR-3 | OVCAR-3 | NHF |
| Cisplatin | 500.000 µM | −12.2 | 1.4 | −33.3 | −2.9 | −64.7 | −23.6 | −48.5 | −7.1 |
| | 250.000 µM | −21.6 | 2.5 | −30.8 | 0.6 | −57.4 | −19.7 | −37.9 | 1.7 |
| | 125.000 µM | −40.1 | −13.4 | −42.2 | 0.1 | −58.9 | −21.8 | −40.9 | −4.2 |
| | 62.500 µM | −22.1 | −43.8 | −33.8 | 1.3 | −53.8 | −24.3 | −45.3 | −3.8 |
| | 31.250 µM | 14.6 | −48.2 | −47.4 | 1.4 | −55.0 | −21.1 | −62.8 | −0.7 |
| | 15.625 µM | 27.5 | 0.0 | −43.2 | 6.9 | 0.5 | −20.3 | −64.6 | 0.2 |
| | 7.812 µM | 38.7 | 3.6 | 15.1 | 21.4 | 11.8 | −14.8 | −73.4 | 27.8 |
| | 3.906 µM | 56.3 | 13.1 | 38.6 | 38.1 | 28.8 | 6.8 | −52.8 | 53.4 |
| | IC$_{50}$ (µM) | N.D. | <3.906 | N.D. | <3.906 | N.D. | <3.906 | N.D. | 4.774 |
| | TGI (µM) | 35.869 | <3.906 | 7.96 | 64.977 | 15.550 | 4.491 | N.D. | 16.139 |
| | LC$_{50}$ (µM) | N.D. | N.D. | N.D. | N.D. | 28.242 | N.D. | 52.739 | N.D. |
| Paclitaxel | 100.000 nM | 24.7 | −25.6 | 69.0 | 5.0 | 4.7 | 13.9 | −57.5 | 16.9 |
| | 50.000 nM | 23.6 | −15.7 | 91.2 | 6.7 | 3.4 | 12.3 | −45.1 | 28.7 |
| | 25.000 nM | 25.7 | −36.7 | 108.2 | 15.1 | 10.1 | 16.8 | −48.7 | 48.9 |
| | 12.500 nM | 29.3 | 8.4 | 112.9 | 24.5 | 17.5 | 68.3 | 31.1 | 58.6 |
| | 6.250 nM | 36.9 | 58.9 | 98.8 | 48.8 | 50.6 | 105.7 | 69.6 | 61.9 |
| | 3.125 nM | 47.6 | 97.3 | 99.4 | 80.8 | 90.9 | 119.4 | 89.6 | 72.1 |
| | 1.562 nM | 65.5 | 95.5 | 96.3 | 99.1 | 96.6 | 112.9 | 90.1 | 79.7 |
| | 0.781 nM | 87.9 | 103.7 | 117.1 | 102.1 | 96.2 | 112.8 | 96.9 | 86.6 |
| | IC$_{50}$ (nM) | 2.817 | 7.197 | N.D. | 6.312 | 6.459 | 14.808 | 10.008 | 18.658 |
| | TGI (nM) | N.D. | 13.021 | N.D. | N.D. | N.D. | N.D. | 15.402 | >100 |
| | LC$_{50}$ (nM) | N.D. | N.D. | N.D. | N.D. | N.D. | N.D. | 35.137 | >100 |

MCF-7: human breast adenocarcinoma cell line; Du-145: human prostate carcinoma cell line; A-375: human malignant melanoma; HT-29: human colorectal adenocarcinoma; HCT 116: human colorectal carcinoma; SK-BR-3: human breast adenocarcinoma; OVCAR-3: human ovarian adenocarcinoma cell line; NHF: human foreskin skin fibroblasts; IC50: Concentration to inhibit 50% of cell growth; TGI: Concentration for total inhibition of cell growth; LC50: Concentration for 50% cell death; N.D.: not determined.

TABLE 2

Results of relative viability and IC50, TGI and LC50 values of the test items against the tumor lines DU-145 and MCF-7.

| Cell line | Concentration | Relative viability (%) of test items | | | | |
|---|---|---|---|---|---|---|
| | | SEQ ID NO. 4 | SEQ ID NO. 9 | SEQ ID NO. 10 | SEQ ID NO. 12 | SEQ CONTROL |
| Du-145 | 100.000 µM | 36.0 | 36.6 | −39.4 | −57.3 | 43.1 |
| | 50.000 µM | 68.4 | 68.0 | 32.5 | −17.5 | 69.9 |
| | 25.000 µM | 88.5 | 82.5 | 72.4 | 50.8 | 74.2 |
| | 12.500 µM | 104.3 | 98.7 | 92.2 | 75.1 | 84.4 |
| | 6.250 µM | 109.6 | 103.6 | 105.3 | 92.2 | 90.3 |
| | 3.125 µM | 104.7 | 106.4 | 104.4 | 99.1 | 93.4 |
| | 1.562 µM | 100.6 | 92.3 | 106.3 | 103.4 | 95.7 |
| | 0.781 µM | 109.3 | 106.1 | 94.8 | 94.0 | 113.4 |
| | IC$_{50}$ (µM) | 72.642 | 74.020 | 39.264 | 23.403 | 89.365 |
| | TGI (µM) | N.D. | >100 | 69.568 | 42.423 | >100 |
| | LC$_{50}$ (µM) | N.D. | N.D. | >100 | 83.501 | >100 |
| MCF-7 | 100.000 µM | 0.7 | −19.5 | −29.0 | −72.5 | 20.0 |
| | 50.000 µM | 43.4 | 37.5 | 25.6 | 2.0 | 31.1 |
| | 25.000 µM | 60.9 | 55.1 | 47.1 | 38.6 | 37.7 |
| | 12.500 µM | 72.7 | 73.6 | 63.0 | 56.5 | 53.6 |
| | 6.250 µM | 86.2 | 84.8 | 74.2 | 67.4 | 59.0 |
| | 3.125 µM | 95.8 | 97.8 | 83.0 | 81.2 | 62.4 |
| | 1.562 µM | 96.7 | 95.5 | 85.8 | 91.5 | 62.8 |
| | 0.781 µM | 110.4 | 103.8 | 86.4 | 87.4 | 54.9 |
| | IC$_{50}$ (µM) | 35.098 | 31.963 | 24.335 | 17.791 | 15.040 |
| | TGI (µM) | >100 | 80.767 | 70.609 | 48.434 | N.D. |
| | LC$_{50}$ (µM) | >100 | >100 | >100 | 84.144 | N.D. |

MCF-7: human breast adenocarcinoma cell line; Du-145: human prostate carcinoma cell line; IC50: Concentration to inhibit 50% of cell growth; TGI: Concentration for total inhibition of cell growth; LC50: Concentration for 50% cell death; N.D.: not determined.

TABLE 3

Results of relative cell viability and IC50, TGI and LC50 values of the test items against tumor lines A-375 and HT-29.

| Cell line | Concentration | Relative cell viability (%) of test items | | | | |
|---|---|---|---|---|---|---|
| | | SEQ ID NO. 4 | SEQ ID NO. 9 | SEQ ID NO. 10 | SEQ ID NO. 12 | SEQ. CONTROL |
| A-375 | 100.000 µM | −72.3 | −19.4 | −72.1 | −79.2 | 46.7 |
| | 50.000 µM | −69.0 | 70.6 | 51.6 | −47.3 | 70.7 |
| | 25.000 µM | 35.7 | 92.5 | 65.8 | 56.3 | 65.4 |
| | 12.500 µM | 85.8 | 97.7 | 81.1 | 85.6 | 81.5 |
| | 6.250 µM | 97.3 | 114.0 | 74.2 | 81.4 | 78.1 |
| | 3.125 µM | 103.0 | 107.0 | 87.7 | 90.4 | 86.2 |
| | 1.562 µM | 100.6 | 107.1 | 84.5 | 92.7 | 92.2 |
| | 0.781 µM | 109.5 | 121.2 | 92.6 | 97.7 | 94.4 |
| | $IC_{50}$ (µM) | 22.748 | 61.116 | 47.908 | 26.263 | >100 |
| | TGI (µM) | 29.656 | 90.397 | 74.279 | 36.326 | >100 |
| | $LC_{50}$ (µM) | 41.088 | >100 | 93.069 | 51.456 | >100 |
| HT-29 | 100.000 µM | −61.1 | 0.2 | −71.9 | −72.1 | 0.2 |
| | 50.000 µM | −84.0 | 14.4 | 15.7 | −44.8 | 5.7 |
| | 25.000 µM | 5.8 | 32.7 | 32.7 | 24.2 | 40.9 |
| | 12.500 µM | 47.4 | 83.1 | 78.3 | 49.4 | 68.8 |
| | 6.250 µM | 74.6 | 92.5 | 94.2 | 81.2 | 73.4 |
| | 3.125 µM | 88.6 | 97.2 | 103.0 | 100.3 | 81.6 |
| | 1.562 µM | 90.7 | 95.9 | 93.7 | 93.5 | 85.3 |
| | 0.781 µM | 93.5 | 92.0 | 90.8 | 93.7 | 91.9 |
| | $IC_{50}$ (µM) | 13.497 | 20.424 | 25.113 | 14.630 | 19.369 |
| | TGI (µM) | 22.932 | N.D. | 53.711 | 30.010 | 81.579 |
| | $LC_{50}$ (µM) | 40.871 | N.D. | 85.816 | 60.311 | N.D. |

Cell lines: A-375: human malignant melanoma; HT-29: human colorectal adenocarcinoma; IC50: Concentration to inhibit 50% of cell growth; TGI: Concentration for total inhibition of cell growth; LC50: Concentration for 50% cell death; N.D.: not determined.

TABLE 4

Results of relative cell viability and IC50, TGI and LC50 values of the test items against the tumor lines HCT 116 and SK-BR-3.

| Cell line | Concentration | Relative cell viability (%) of test items | | | | |
|---|---|---|---|---|---|---|
| | | SEQ ID NO. 4 | SEQ ID NO. 9 | SEQ ID NO. 10 | SEQ ID NO. 12 | SEQ. CONTROL |
| HCT 116 | 100.000 µM | −70.2 | −19.5 | −47.3 | −55.9 | 0.1 |
| | 50.000 µM | 3.6 | 11.5 | 6.3 | 1.3 | 10.0 |
| | 25.000 µM | 24.4 | 33.3 | 27.9 | 17.4 | 29.4 |
| | 12.500 µM | 57.1 | 72.2 | 69.4 | 56.5 | 49.0 |
| | 6.250 µM | 85.0 | 88.9 | 96.1 | 84.0 | 59.6 |
| | 3.125 µM | 85.5 | 87.9 | 99.9 | 105.2 | 80.9 |
| | 1.562 µM | 95.4 | 94.6 | 97.5 | 93.2 | 86.8 |
| | 0.781 µM | 103.6 | 99.9 | 95.9 | 98.0 | 89.0 |
| | $IC_{50}$ (µM) | 16.790 | 20.100 | 20.210 | 15.983 | 11.261 |
| | TGI (µM) | 45.410 | 58.519 | 47.447 | 41.730 | 97.076 |
| | $LC_{50}$ (µM) | 84.372 | N.D. | >100 | 96.324 | N.D. |
| SK-BR-3 | 100.000 µM | −86.3 | −70.0 | −66.5 | −77.1 | −27.4 |
| | 50.000 µM | −34.6 | 3.1 | −8.6 | −36.3 | 14.4 |
| | 25.000 µM | 47.0 | 48.7 | 50.2 | 53.1 | 47.3 |
| | 12.500 µM | 96.1 | 98.5 | 90.0 | 84.3 | 79.5 |
| | 6.250 µM | 106.2 | 109.1 | 95.4 | 103.3 | 79.1 |
| | 3.125 µM | 98.6 | 111.1 | 113.9 | 117.5 | 86.9 |
| | 1.562 µM | 103.4 | 99.9 | 99.1 | 109.9 | 85.7 |
| | 0.781 µM | 101.9 | 107.5 | 98.0 | 102.2 | 89.4 |
| | $IC_{50}$ (µM) | 24.953 | 28.316 | 25.981 | 24.313 | 25.701 |
| | TGI (µM) | 37.515 | 49.017 | 45.137 | 37.529 | 61.419 |
| | $LC_{50}$ (µM) | 56.934 | 80.714 | 78.599 | 60.225 | >100 |

Cell lines: HCT 116: human colorectal carcinoma; SK-BR-3: Human breast adenocarcinoma; IC50: Concentration to inhibit 50% of cell growth; TGI: Concentration for total inhibition of cell growth; LC50: Concentration for 50% cell death; N.D.: not determined.

TABLE 5

Results of relative cell viability and IC50, TGI and LC50 values of the test items against the OVCAR-3 and NHF cell lines.

| Cell line | Concentration | Relative viability (%) of test items | | | | |
|---|---|---|---|---|---|---|
| | | SEQ ID NO. 4 | SEQ ID NO. 9 | SEQ ID NO. 10 | SEQ ID NO. 12 | SEQ CONTROL |
| OVCAR-3 | 100.000 μM | −68.1 | −62.0 | −51.1 | −57.9 | −7.7 |
| | 50.000 μM | −14.6 | 8.1 | −3.7 | −18.5 | 12.0 |
| | 25.000 μM | 37.7 | 23.4 | 16.9 | 27.5 | 31.5 |
| | 12.500 μM | 48.0 | 50.2 | 34.7 | 38.4 | 56.7 |
| | 6.250 μM | 67.2 | 84.3 | 59.2 | 65.8 | 80.2 |
| | 3.125 μM | 89.4 | 93.9 | 77.9 | 75.0 | 82.0 |
| | 1.562 μM | 93.9 | 99.6 | 90.2 | 87.7 | 87.2 |
| | 0.781 μM | 99.6 | 105.9 | 79.9 | 81.8 | 99.2 |
| | $IC_{50}$ (μM) | 14.235 | 16.093 | 9.455 | 11.088 | 15.619 |
| | TGI (μM) | 41.931 | 45.952 | 39.740 | 37.711 | 72.599 |
| | $LC_{50}$ (μM) | 82.361 | 91.419 | >100 | 87.809 | N.D. |
| NHF | 100.000 μM | −25.4 | −12.8 | −32.9 | −54.1 | −49.2 |
| | 50.000 μM | 19.8 | 44.6 | 24.3 | 8.8 | 19.4 |
| | 25.000 μM | 73.4 | 84.6 | 66.8 | 70.0 | 60.5 |
| | 12.500 μM | 106.6 | 114.0 | 101.4 | 101.4 | 98.3 |
| | 6.250 μM | 100.7 | 92.7 | 96.1 | 109.0 | 99.5 |
| | 3.125 μM | 98.4 | 95.7 | 93.5 | 97.7 | 107.4 |
| | 1.562 μM | 94.2 | 96.2 | 101.8 | 99.8 | 113.8 |
| | 0.781 μM | 95.3 | 104.0 | 103.3 | 99.4 | 107.7 |
| | $IC_{50}$ (μM) | 35.554 | 46.864 | 35.702 | 33.728 | 32.629 |
| | TGI (μM) | 63.101 | 83.697 | 64.820 | 53.452 | 60.658 |
| | $LC_{50}$ (μM) | N.D. | N.D. | >100 | 93.611 | >100 |

OVCAR-3: human ovarian adenocarcinoma cell line; NHF: human foreskin skin fibroblasts; IC50: Concentration to inhibit 50% of cell growth; TGI: Concentration for total inhibition of cell growth; LC50: Concentration for 50% cell death; N.D.: not determined.

Table 6 shows the cell viability results obtained for the test item SEQ ID NO. 12 compared to the cell viability results of the same test item associated with the reference item cisplatin at a concentration of 3 μM. At this concentration, the cisplatin reference item showed a relative cell viability of 19.1%.

TABLE 6

Viability results of the OVCAR-3 cell line in the synergism test.

| | Relative viability (%) | |
|---|---|---|
| Concentration | SEQ ID NO. 12 | SEQ ID NO. 12 + Cisplatin |
| 100,000 μM | −57.9 | −67.9 |
| 50,000 μM | −18.5 | −64.9 |
| 25,000 μM | 27.5 | 5.3 |
| 12,500 μM | 38.4 | 7.7 |
| 6,250 μM | 65.8 | 11.5 |
| 3,125 μM | 75.0 | 13.9 |
| 1,562 μM | 87.7 | 15.0 |

As can be seen, Table 6 presents the results of the cellular viability of the aptamer SEQ. ID NO 12 when associated with cisplatin, a reference drug in cancer therapy. It is possible to observe that the SEQ. ID NO 10 substantially improved the antiproliferative activity profile against the OVCAR-3 cell line, in comparison to both the aptamer and cisplatin profiles, both individually evaluated. This data highlights the considerable and innovative therapeutic potential of SEQ. ID NO 12 as a disruptive synergistic agent in cancer therapy.

All put together, the present data makes the point that DNA aptamers, as anti-galectin inhibitors, represent a promising innovative approach in cancer therapy, in particular to those which display a high metastasis and angiogenesis rate associated with high hGal1 expression. In this way, galectin inhibitors may restore the immunological system sensitivity against cancer cells, and thus, act as synergistic drugs in oncology therapy.

Numerous reports describe that high hGal1 expression is highly associated with a poor prognostic criterion, as low survival rate or cytotoxic drug resistance in many human cancers.

New approaches in oncology therapy, such as combination therapies are crucial in the future clinical development of galectin-1 inhibitors strategies. Synergistic effects between reference therapeutics drugs, like cisplatin, and DNA aptamers, as described in table 6, are a disruptive approach in cancer treatment, and will be of tremendous impact in combination therapies, improving on going oncology protocols treatments. In the present invention is notably demonstrated that besides DNA aptamers stand-alone in vitro treatment displays unequivocal antiproliferative effects in several cancer cell lines with much higher effectiveness over traditional antigalectin compounds, its association with preferred chemotherapy drugs, such as cisplatin among others, is an encouraging way to positioning these molecules in clinical development.

The data presented here for SEQ. NO 12 support the validness of using these new class of galectin-1 inhibitor as a novel and promising clinical approach to inhibit cancer cell proliferation, while also enhancing the efficiency of a current anticancer drug when used in association.

The aptamer SEQ ID NO 12 when associated with the reference item cisplatin at a concentration of 3 μM, potentiated the profile of antiproliferative activity against the cell line OVCAR-3 when compared to the profile of this same test item evaluated individually. Cisplatin alone has 19.1% cell viability for OVCAR-3 strain, at a concentration of 3 μM, and when associated with SEQ ID NO 4, it is at a concentration of 12.5 μM, the cell viability of the composition drops to 7, 7%, a decrease of almost 60%. Thus, the aptamer enhances the antiproliferative activity profile of cisplatin against the OVCAR-3 cell line, showing the synergistic effect of that with cisplatin, a reference drug in oncology.

It is important to note that the same cell line, when evaluated alone with SEQ ID NO 4 at a concentration of 12.5 µM, showed cell viability of 38.4%. Thus, the synergistic effect occurs in both the aptamer for cisplatin and the latter for the aptamer.

According to the results:
Concentrations between 15 and 35 µM of aptamers promoted 50% inhibition of the growth of the MCF-7 cell line, while concentrations between 23 and 89 µM of the test items promoted a 50% reduction in cell growth of the Du-145 cell line;
Concentrations between 22.7 µM and 61.1 µM of aptamers promoted 50% inhibition of cell line A-375 growth, whereas concentrations between 13.5 and 25.1 µM of test items reduced 50% cell growth of the HT-29 strain;
Concentrations between 11.2 µM and 20.2 µM of aptamers inhibited 50% of the growth of the HCT 116 cell line and concentrations between 24 µM and 25 µM of the test items promoted a 50% reduction in the cell growth of the SK-BR-3;
Concentrations between 37 and 72 µM of aptamers promoted total growth inhibition of the OVCAR-3 cell line, while concentrations between 53 and 83 µM of the test items promoted total growth inhibition of the NHF cell line;
The aptamer SEQ ID NO. 12 when associated with the reference item cisplatin at a concentration of 3 µM, potentiated the profile of antiproliferative activity against the cell line OVCAR-3 when compared to the profile of this same test item evaluated individually.

According to the experimental conditions and methodologies used in the present study, it is concluded for the test items SEQ ID NO. 4, SEQ ID NO. 9, SEQ ID NO. 10, SEQ ID NO. 12 and SEQ CONTROL:

A: General Conclusions:
I. The test items SEQ ID NO. 4, SEQ ID NO. 9, SEQ ID NO. 10, SEQ ID NO. 12 and SEQ CONTROL reduce the viability of human tumor lines SK-BR-3, MCF-7, DU-145, OVCAR-3, HT-29, HCT-116, A-375 and the non-tumor line NHF as a function of the analyzed concentration.

B: Specific Conclusions
I. The test items show more intense antiproliferative/cytotoxic activity in tumor lines than in normal cells;
II. The test item SEQ. ID NO.:12 enhances the profile of cisplatin's antiproliferative activity against the OVCAR-3 cell line.

Molecular Modeling

In order to predict the 3D structure of the ssDNA aptamer (SEQ ID NO. 4) the overall protocol described was followed:

The secondary structure of the aptamer was predicted by the Mfold webserver using temperature of 25° C. and ionic strength derived from the PBS buffer, 0.195 mol/L, to mimic the experimental folding conditions. Three possibilities for the secondary structure were retrieved and used as input for the RNA composer webserver that predicts the 3D structure of RNA aptamers. The output structures were converted to DNA by methylation of all Uracil nucleobases to turn them into Thymines and by removing the 2' hydroxyl group from all riboses.

The initial structure for the human Galectin-1 protein was taken from PDB ID 1GZW. All ligands and water molecules were removed. Hydrogens were added to both the protein and the DNA aptamer using GROMACS 2016.3 and docking was performed using the NPDock webserver, which is specialized in nucleic acid-protein docking.

Figure 13A:
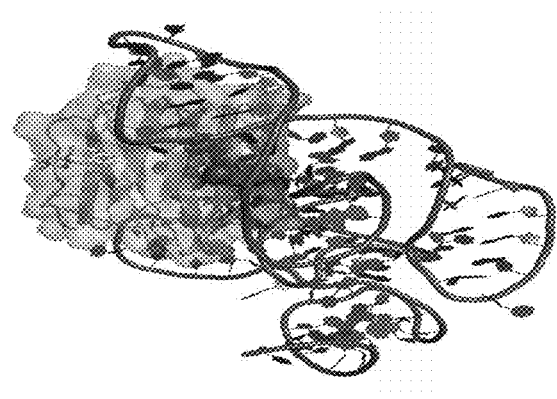
FIG. 13 illustrates the putative binding mode between hGal-1 and SEQ ID NO.: 4. The protein is shown as green cartoon with surface with the hydrophobic dimerization interface highlighted in gray. Galactose is shown as yellow sticks, Glucose is shown as orange sticks, solvent exposed cysteine side chains are shown as red spheres and the aptamer is shown as blue cartoon; wherein FIG. 13 A illustrates an angle showing the carbohydrate recognition site.
FIG. 13B illustrates an angle showing the dimerization interface.
FIG. 13C illustrates an angle showing the interaction between the cysteine side chains and the aptamer.
Figure 13B:
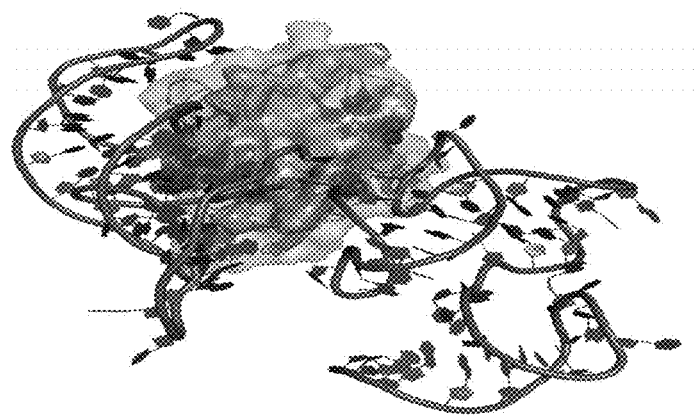
Figure 13C:
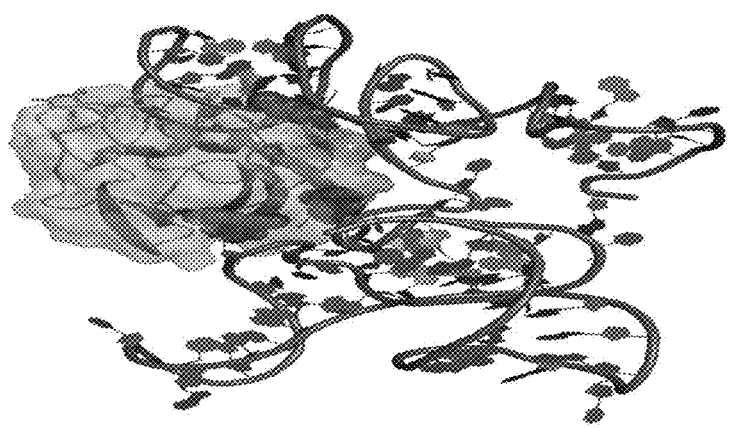
Figure 14A:
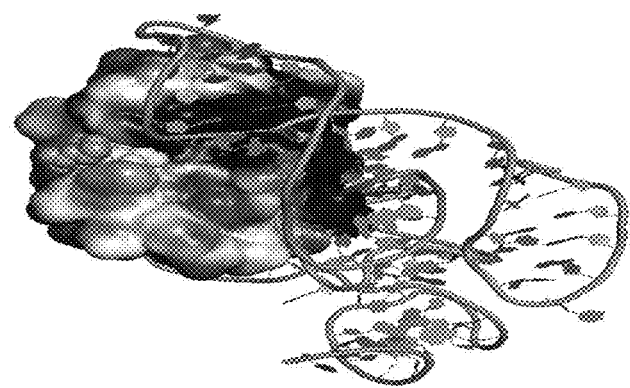
FIG. 14A illustrates an angle showing the carbohydrate recognition site.
Figure 14B:
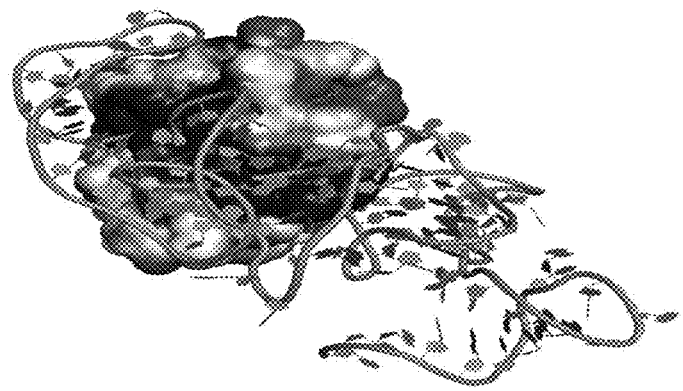
FIG. 14B illustrates an angle showing the dimerization interface and FIG. 14C illustrates an angle showing the interaction between the cysteine side chains and the aptamer.
Figure 14C:
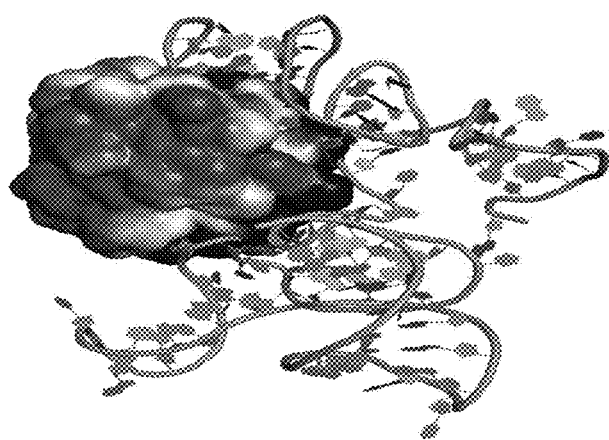

FIGS. 13 and 14 were made with open source PyMOL 1.8.6.0 and the electrostatic potential was calculated with APBS.

Results & Discussion of the Molecular Modeling

Docking calculations revealed a putative binding mode between the aptamer and the monomeric form of hGal-1 that provides a molecular mechanism for the experimentally observed effects of their interaction. According to this putative binding mode, the aptamer-protein interaction involves the hydrophobic dimerization interface of the monomer (FIG. 13A and FIG. 13B). This is in agreement with experimental data from ThermoFluor showing that there is increased hydrophobic area exposure when the aptamer is added to a solution of hGal-1. This interaction mode also explains the observed anti-hemagglutination activity because, even though the carbohydrate recognition site is not disrupted by the presence of the aptamer, it blocks the dimerization interface leads to disruption of the galectin networks that would result in hemagglutination.

It was observed that treating hGal-1 with Iodoacetamide, which covalently binds the acetamide group in all solvent accessible cysteines sulfhydryl side chain, abolishes the anti-hemagglutinating activity of the aptamer. According to the proposed binding mode, this happens because Cysteines 2, 88 and 130 interact directly with the aptamer and adding the acetamide group to their side chains would disrupt specific aptamer-protein interactions (FIG. 13C). The only solvent accessible cysteine that does not interact with the aptamer is Cys-16. Interestingly, excellent physicochemical complementarity was observed: the aptamer, which is negatively charged, interacts only with the sites of hGal-1 which have positive electrostatic potential (FIG. 14).

The molecular modeling was used to suggest that the molecular interaction between hGal-1 and aptamer 4 involves the dimerization interface of the monomer of hGal-1. This putative binding mode agrees with all experimental data about the aptamer-protein recognition.

Uses of the Developed Aptamers

It appears that the discovery of such potential new hGal1 inhibitors will help in the development of new diagnostic strategies and therapeutic strategies for diseases correlated with hGal1. Thus, the aptamers developed can be used in the treatment of a disorder relating to the binding of human galectin-1 to a ligand in a mammal, wherein said disorder is selected from the group consisting of inflammation, fibrosis, septic shock, cancer, autoimmune diseases, metabolic disorders, heart disease, heart failure, pathological angiogenesis, as neovascularization related to cancer, and eye diseases.

The cancer is selected from the group consisting of ovarian cancer, squamous cell carcinoma, a cancer of the digestive system, stomach cancer, liver cancer, colon cancer, a cancer of the thyroid, a cancer of the endometrium, adenocarcinoma of the endometrium, uterine cancer, uterine adenocarcinoma, a uterine smooth muscle tumor, breast cancer, prostate cancer, bladder cancer, a head cancer, a neck cancer, a glioma, a kidney cancer, pancreatic cancer, pancreatic ductal adenocarcinoma, nonsmall-cell lung cancer, and melanoma.

Additionally, it is worth noting that the majority of aptamers still has the ability to inhibit the cancer growth process, namely metastasis, that is also related to human galectin-1.

The invention claimed is:

1. Aptamers of nucleic acid comprising formula (1)

AGCTGACACAGCAGGTTGGTGCXan$_1$Xan$_2$Xan$_3$Xan$_4$Xan$_5$Xan$_6$Xan$_7$

Xan$_8$Xan$_9$Xan$_{10}$Xan$_{11}$Xan$_{12}$Xan$_{13}$Xan$_{14}$Xan$_{15}$Xan$_{16}$Xan$_{17}$Xan$_{18}$

Xan$_{19}$Xan$_{20}$Xan$_{21}$Xan$_{22}$Xan$_{23}$Xan$_{24}$Xan$_{25}$Xan$_{26}$Xan$_{27}$Xan$_{28}$Xan$_{29}$

Xan$_{30}$Xan$_{31}$Xan$_{32}$Xan$_{33}$Xan$_{34}$Xan$_{35}$Xan$_{36}$Xan$_{37}$Xan$_{38}$Xan$_{39}$Xan$_{40}$

Xan$_{41}$Xan$_{42}$Xan$_{43}$Xan$_{44}$Xan$_{45}$Xan$_{46}$Xan$_{47}$Xan$_{48}$Xan$_{49}$Xan$_{50}$Xan$_{51}$

Xan$_{52}$CCGAGTCGAGCAATCTCGAAAT formula (1) (SEQ ID NO: 46)
wherein:
Xan$_1$, Xan$_6$, Xan$_7$, Xan$_8$, Xan$_9$, Xan$_{10}$, Xan$_{11}$, Xan$_{12}$, Xan$_{16}$, Xan$_{17}$, Xan$_{18}$, Xan$_{26}$, Xan$_{28}$, Xan$_{29}$, Xan32, Xan$_{34}$, Xan$_{35}$, Xan$_{36}$, Xan$_{40}$, Xan$_{41}$, Xan$_{42}$, Xan$_{48}$, Xan$_{49}$, Xan$_{50}$, Xan$_{51}$ and Xan$_{52}$ are A, T, C, G or absent;
Xan$_2$, Xan$_3$, Xan$_4$, Xan$_5$, Xan$_{13}$, Xan$_{14}$, Xan$_{15}$, Xan$_{19}$, Xan$_{20}$, Xan$_{21}$, Xan$_{22}$, Xan$_{23}$, Xan$_{24}$, Xan$_{25}$, Xan$_{27}$, Xan$_{30}$, Xan$_{31}$, Xan$_{33}$, Xan$_{37}$, Xan$_{38}$, Xan$_{39}$, Xan$_{43}$, Xan$_{44}$ and Xan$_{45}$ are A, T, C, G;
Xan$_{46}$ is A, T, C or absent; and
Xan$_{47}$ is T, C, G or absent,
wherein the aptamers are chemically modified or not.

2. Aptamers according to claim 1, wherein the sequence of formula 1 is represented by any one of SEQ ID NO: 1 to SEQ ID NO: 20 or variants thereof with the same or highly similar tertiary structure that bind to the amino acid sequence SEQ ID NO. 42.

3. Aptamers according to claim 1, wherein the aptamers inhibit the binding of human Galectin-1 to a ligand in a human, and or inhibiting the human Galectin-1 dimer formation, and/or causing the dissociation of human Galectin-1 dimeric form.

4. A method for treating a disorder relating to the binding of human galectin-1 to a ligand in a human, wherein said disorder is cancer, the method comprising administering the aptamers according to claim 1.

5. The method according to claim 4, wherein the pathological angiogenesis is neovascularization related to cancer.

6. The method according to claim 4, wherein the cancer is selected from the group consisting of ovarian cancer, squamous cell carcinoma, a cancer of the digestive system, stomach cancer, liver cancer, colon cancer, a cancer of the thyroid, a cancer of the endometrium, adenocarcinoma of the endometrium, uterine cancer, uterine adenocarcinoma, a uterine smooth muscle tumor, breast cancer, prostate cancer, bladder cancer, a head cancer, a neck cancer, a glioma, a kidney cancer, pancreatic cancer, pancreatic ductal adenocarcinoma, nonsmall-cell lung cancer, and melanoma.

7. A method for inhibiting human Galectin-1, wherein the method comprises contacting a human cancer cell with an effective amount of a galectin-1-targeting compound comprising the aptamers according to claim 1.

8. The method of claim 7, wherein said aptamers have an affinity for the hydrophobic dimerization interface of galectin-1.

9. The method of claim 7, wherein the method inhibits growth of the human cancer cell, proliferation of the human cancer cell, and/or inhibits tumor metastasis.

10. The method of claim 7, wherein the method comprises the association of the galectin-1 targeting compound with chemotherapy drugs.

11. A method for treating cancer in a human in need thereof comprising administering a therapeutically effective amount of aptamers according to claim 1.

12. Aptamers of nucleic acid comprising formula (2)

AGCTGACACAGCAGGTTGGTGCXan$_1$Xan$_2$Xan$_3$Xan$_4$Xan$_5$AXan$_6$Xan$_7$

Xan$_8$Xan$_9$Xan$_{10}$Xan$_{11}$Xan$_{12}$Xan$_{13}$Xan$_{14}$Xan$_{15}$Xan$_{16}$Xan$_{17}$Xan$_{18}$

Xan$_{19}$Xan$_{20}$Xan$_{21}$Xan$_{22}$Xan$_{23}$Xan$_{24}$Xan$_{25}$Xan$_{26}$Xan$_{27}$Xan$_{28}$Xan$_{29}$

Xan$_{30}$Xan$_{31}$Xan$_{32}$Xan$_{33}$Xan$_{34}$Xan$_{35}$Xan$_{36}$Xan$_{37}$Xan$_{38}$Xan$_{39}$Xan$_{40}$

Xan$_{41}$Xan$_{42}$Xan$_{43}$Xan$_{44}$AXan$_{45}$Xan$_{46}$Xan$_{47}$Xan$_{48}$CCGAGTCGAGCAA

TCTCGAAAT formula (2) (SEQ ID NO: 47)
wherein:
Xan$_1$ and Xan$_{45}$ are C or is absent;
Xan$_2$, Xan$_{14}$, Xan$_{17}$, Xan$_{27}$, Xan$_{30}$, Xan$_{34}$, Xan$_{36}$ and Xan$_{48}$ are A, C or G;
Xan$_3$, Xan$_4$, Xan$_9$, Xan$_{10}$, Xan$_{16}$, Xan$_{25}$, Xan$_{33}$ and Xan$_{40}$ are A or C;
Xan$_5$, Xan$_7$, Xan$_{20}$, Xan$_{22}$, Xan$_{32}$, Xan$_{37}$ and Xan$_{38}$ are A, C or T;
Xan$_6$, Xan$_8$, Xan$_{11}$, Xan$_{29}$, Xan$_{41}$ and Xan$_{47}$ are A or G;
Xan$_{12}$, Xan$_{24}$, Xan$_{31}$ and Xan$_{46}$ are A, G or T;
Xan$_{15}$, Xan$_{21}$, Xan$_{23}$ and Xan$_{35}$ are C or G;
Xan$_{18}$ and Xan$_{43}$ are G or T;
Xan$_{19}$, Xan$_{39}$ and Xan$_{44}$ are A or T;
Xan$_{26}$ and Xan$_{42}$ are C, G or T;
Xan$_{28}$ is C or T,
wherein the aptamers are chemically modified or not.

13. Aptamers according to claim 12, wherein the sequence of formula 2 is represented by any one of SEQ ID NO: 4, 9, 10 and 12 or variants thereof with the same or highly similar tertiary structure that bind to the amino acid sequence SEQ ID NO. 42.

14. Aptamers according to claim 12, wherein the aptamers inhibit the binding of human Galectin-1 to a ligand in a human; inhibit the human Galectin-1 dimer formation; and/or cause the dissociation of human Galectin-1 dimeric form.

15. A method for treating a disorder relating to the binding of human galectin-1 to a ligand in a human, wherein said disorder is cancer, the method comprising administering the aptamers according to claim 12.

16. The method according to claim 15, wherein the pathological angiogenesis is neovascularization related to cancer.

17. The method according to claim 15, wherein the cancer is selected from the group consisting of ovarian cancer, squamous cell carcinoma, a cancer of the digestive system, stomach cancer, liver cancer, colon cancer, a cancer of the thyroid, a cancer of the endometrium, adenocarcinoma of the endometrium, uterine cancer, uterine adenocarcinoma, a uterine smooth muscle tumor, breast cancer, prostate cancer, bladder cancer, a head cancer, a neck cancer, a glioma, a kidney cancer, pancreatic cancer, pancreatic ductal adenocarcinoma, nonsmall-cell lung cancer, and melanoma.

18. A method for inhibiting human Galectin-1, wherein the method comprises contacting a human cancer cell with an effective amount of a galectin-1-targeting compound comprising the aptamers according to claim 12.

19. The method of claim 18, wherein said aptamers have an affinity for the hydrophobic dimerization interface of galectin-1.

20. The method of claim 18, wherein the method inhibits growth of the human cancer cell, proliferation of the human cancer cell, and/or inhibits tumor metastasis.

21. The method of claim 18, wherein the method comprises the association of the galectin-1 targeting compound with chemotherapy drugs.

22. A method for treating cancer in a human in need thereof comprising administering a therapeutically effective amount of aptamers according to claim 12.

23. Aptamers of nucleic acid comprising formula (3)

ATTTCGAGATTGCTCGACTCGGXan$_1$Xan$_2$Xan$_3$Xan$_4$Xan$_5$Xan$_6$Xan$_7$

Xan$_8$Xan$_9$Xan$_{10}$Xan$_{11}$Xan$_{12}$Xan$_{13}$Xan$_{14}$Xan$_{15}$Xan$_{16}$Xan$_{17}$Xan$_{18}$

Xan$_{19}$Xan$_{20}$Xan$_{21}$Xan$_{22}$Xan$_{23}$Xan$_{24}$Xan$_{25}$Xan$_{26}$Xan$_{27}$Xan$_{28}$Xan$_{29}$

Xan$_{30}$Xan$_{31}$Xan$_{32}$Xan$_{33}$Xan$_{34}$Xan$_{35}$Xan$_{36}$Xan$_{37}$Xan$_{38}$Xan$_{39}$Xan$_{40}$

Xan$_{41}$Xan$_{42}$Xan$_{43}$Xan$_{44}$Xan$_{45}$Xan$_{46}$Xan$_{47}$Xan$_{48}$Xan$_{49}$Xan$_{50}$Xan$_{51}$

GCACCAACCTGCTGTGTCAGCT formula (3) (SEQ ID NO: 48)
wherein:
Xan$_1$, Xan$_2$, Xan$_5$, Xan$_6$, Xan$_{15}$, Xan$_{22}$, Xan$_{23}$, Xan$_{34}$, Xan$_{35}$, Xan$_{49}$, Xan$_{50}$ and Xan$_{51}$ are A, T, C, G or absent;
Xan$_3$, Xan$_4$, Xan$_7$, Xan$_8$, Xan$_9$, Xan$_{10}$, Xan$_{11}$, Xan$_{12}$, Xan$_{13}$, Xan$_{14}$, Xan$_{16}$, Xan$_{17}$, Xan$_{18}$, Xan$_{19}$, Xan$_{20}$, Xan$_{24}$, Xan$_{25}$, Xan$_{26}$, Xan$_{27}$, Xan$_{28}$, Xan$_{29}$, Xan$_{30}$, Xan$_{31}$, Xan$_{32}$, Xan$_{33}$, Xan$_{36}$, Xan$_{37}$, Xan$_{38}$, Xan$_{39}$, Xan$_{40}$, Xan$_{41}$, Xan$_{42}$, Xan$_{43}$, Xan$_{44}$, Xan$_{45}$, Xan$_{46}$ and Xan$_{48}$ are A, T, C, G;
Xan$_{21}$ is C, G or T; and
Xan$_{47}$ is A, G or T,
wherein the aptamers are chemically modified or not.

24. Aptamers according to claim 23, wherein the sequence of formula 3 is represented by any one of SEQ ID NO: 21 to SEQ ID NO: 41 or variants thereof with the same or highly similar tertiary structure that bind to the amino acid sequence SEQ ID NO. 42.

25. Aptamers according to claim 23, wherein the aptamers inhibit the binding of human Galectin-1 to a ligand; inhibit the human Galectin-1 dimer formation; and/or cause the dissociation of human Galectin-1 dimeric form.

26. A method for treating a disorder relating to the binding of human galectin-1 to a ligand in a human, wherein said disorder is cancer, the method comprising administering the aptamers according to claim 23.

27. The method according to claim 26, wherein the pathological angiogenesis is neovascularization related to cancer.

28. The method according to claim 26, wherein the cancer is selected from the group consisting of ovarian cancer, squamous cell carcinoma, a cancer of the digestive system, stomach cancer, liver cancer, colon cancer, a cancer of the thyroid, a cancer of the endometrium, adenocarcinoma of the endometrium, uterine cancer, uterine adenocarcinoma, a uterine smooth muscle tumor, breast cancer, prostate cancer, bladder cancer, a head cancer, a neck cancer, a glioma, a kidney cancer, pancreatic cancer, pancreatic ductal adenocarcinoma, nonsmall-cell lung cancer, and melanoma.

29. A method for inhibiting human Galectin-1, wherein the method comprises contacting a human cancer cell with an effective amount of a galectin-1-targeting compound comprising the aptamers according to claim 23.

30. The method of claim 29, wherein said aptamers have an affinity for the hydrophobic dimerization interface of galectin-1.

31. The method of claim 29, wherein the method inhibits growth of the human cancer cell, proliferation of the human cancer cell, and/or inhibits tumor metastasis.

32. The method of claim 29, wherein the method comprises the association of the galectin-1 targeting compound with chemotherapy drugs.

33. A method for treating cancer in a human in need thereof comprising administering a therapeutically effective amount of aptamers according to claim 23.

34. A nucleotide sequence being at least 80% or more, similar to a nucleotide sequence selected from SEQ ID NOs. 1 to 41 or variants thereof or highly similar to their tertiary structure that bind specifically to the amino acid sequence SEQ ID NO. 42 (hGal1), with an affinity (Kd) of less than 70 uM.

* * * * *